US012697129B2

(12) United States Patent
Anderson et al.

(10) Patent No.: US 12,697,129 B2
(45) Date of Patent: *Aug. 4, 2026

(54) DRIVING DEVICES AND METHODS FOR DETERMINING MATERIAL STRENGTH IN REAL-TIME

(71) Applicant: Quartus Engineering Incorporated, San Diego, CA (US)

(72) Inventors: Wayne Anderson, Malibu, CA (US); John J. Perry, Malibu, CA (US); Michael M. Karch, Malibu, CA (US); Anthony D. Truscott, Las Vegas, NV (US); Edward J. Dohring, Malibu, CA (US)

(73) Assignee: Quartus Engineering Incorporated, San Diego, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 18/501,223

(22) Filed: Nov. 3, 2023

(65) Prior Publication Data

US 2024/0058016 A1 Feb. 22, 2024

Related U.S. Application Data

(60) Continuation of application No. 16/915,063, filed on Jun. 29, 2020, now Pat. No. 11,839,385, which is a
(Continued)

(51) Int. Cl.
A61B 17/16 (2006.01)
A61B 17/17 (2006.01)
(Continued)

(52) U.S. Cl.
CPC ...... A61B 17/1622 (2013.01); A61B 17/1624 (2013.01); A61B 17/1626 (2013.01);
(Continued)

(58) Field of Classification Search
CPC . A61B 17/16; A61B 17/1613; A61B 17/1622; A61B 17/1624; A61B 17/1626; A61B 17/1633; A61B 17/17
See application file for complete search history.

(56) References Cited

U.S. PATENT DOCUMENTS

| | | | |
|---|---|---|---|
| 1,308,798 A | 7/1919 | Masland | |
| 1,831,813 A | 11/1931 | Levedahl | |

(Continued)

FOREIGN PATENT DOCUMENTS

| | | | |
|---|---|---|---|
| CN | 1688258 A | 10/2005 | |
| CN | 2774405 Y | 4/2006 | |

(Continued)

OTHER PUBLICATIONS http://www.motion-control-info.com/encoder_design_guide.html. Web. Aug. 20, 2009. 8 pages.
(Continued)

*Primary Examiner* — Larry E Waggle, Jr.
(74) *Attorney, Agent, or Firm* — Snell & Wilmer, L.L.P.; April Wurster

(57) ABSTRACT

A system including an instrument having a working tool configured to penetrate a tissue; a sensor configured to generate in real-time one or more torque signals related to torque of the working tool; a controller in operative communication with the sensor and configured to receive the one or more torque signals. The controller processes the torque signals into one or more processed signals representative of torque, energy, power or a combination thereof. The system also includes a display providing to the user in real-time the one or more processed signals. Related devices, systems, methods, and articles are provided.

18 Claims, 21 Drawing Sheets

Related U.S. Application Data division of application No. 16/077,021, filed as application No. PCT/US2017/017517 on Feb. 10, 2017, now Pat. No. 10,736,643.

(60) Provisional application No. 62/294,717, filed on Feb. 12, 2016.

(51) Int. Cl.
| | |
|---|---|
| *G01L 3/08* | (2006.01) |
| *G01L 3/10* | (2006.01) |
| *G01L 3/14* | (2006.01) |
| *A61B 90/00* | (2016.01) |

(52) U.S. Cl.
CPC .......... *A61B 17/1633* (2013.01); *A61B 17/17* (2013.01); *G01L 3/08* (2013.01); *G01L 3/10* (2013.01); *G01L 3/1478* (2013.01); *A61B 2090/066* (2016.02)

(56) References Cited

U.S. PATENT DOCUMENTS

| | | | |
|---|---|---|---|
| 2,488,992 A | 11/1949 | Taylor | |
| 2,557,429 A | 6/1951 | Hawley | |
| 2,837,939 A * | 6/1958 | Leitner | B25H 1/0078 |
| | | | 408/110 |
| 2,849,900 A * | 9/1958 | Heidtman, Jr. | B25H 1/0078 |
| | | | 408/112 |
| 2,869,403 A | 1/1959 | Bent | |
| 2,883,891 A | 4/1959 | Shutlers et al. | |
| 2,909,949 A | 10/1959 | Winslow | |
| 2,997,900 A * | 8/1961 | Pugsley | B25H 1/0021 |
| | | | 408/112 |
| 3,083,593 A | 4/1963 | Cotter | |
| 3,397,600 A | 8/1968 | Wells | |
| 3,526,158 A | 9/1970 | Adams et al. | |
| 3,546,976 A | 12/1970 | Clapp et al. | |
| 3,750,671 A | 8/1973 | Hedrick | |
| 3,775,021 A | 11/1973 | Langebach | |
| 3,854,836 A | 12/1974 | Weissman | |
| 3,867,932 A | 2/1975 | Huene | |
| 4,005,527 A | 2/1977 | Wilson et al. | |
| 4,010,943 A * | 3/1977 | Eft | B25H 1/0064 |
| | | | 408/712 |
| 4,111,208 A | 9/1978 | Leuenberger | |
| 4,157,231 A | 6/1979 | Phillips | |
| 4,209,069 A | 6/1980 | Smith | |
| 4,242,017 A | 12/1980 | De Fazio | |
| 4,288,182 A | 9/1981 | Vandenkieboom et al. | |
| 4,329,092 A | 5/1982 | Ponitzsch et al. | |
| 4,341,206 A | 7/1982 | Perrett et al. | |
| 4,351,467 A | 9/1982 | White | |
| 4,358,228 A | 11/1982 | Stark | |
| 4,440,529 A | 4/1984 | Henslee et al. | |
| 4,461,015 A | 7/1984 | Kulhavy | |
| 4,487,270 A | 12/1984 | Huber | |
| 4,534,420 A | 8/1985 | Goldelius | |
| 4,594,030 A | 6/1986 | Weigel, Jr. | |
| 4,601,518 A | 7/1986 | Laneus | |
| 4,620,539 A | 11/1986 | Andrews et al. | |
| 4,644,335 A | 2/1987 | Wen | |
| 4,688,970 A | 8/1987 | Eckman | |
| 4,710,075 A | 12/1987 | Davison | |
| 4,723,911 A | 2/1988 | Kurtz | |
| 4,728,876 A | 3/1988 | Mongeon et al. | |
| 4,736,742 A | 4/1988 | Alexson et al. | |
| 4,749,314 A | 6/1988 | LeBlond | |
| 4,752,161 A | 6/1988 | Hill | |
| 4,852,434 A | 8/1989 | Bald | |
| 4,854,786 A | 8/1989 | Alexander et al. | |
| 4,854,873 A | 8/1989 | Linden | |
| 4,961,674 A | 10/1990 | Wang et al. | |
| 5,014,793 A | 5/1991 | Germanton et al. | |
| 5,071,293 A | 12/1991 | Wells | |
| 5,405,348 A | 4/1995 | Anspach, Jr. et al. | |
| 5,409,493 A | 4/1995 | Greenberg | |
| 5,411,503 A | 5/1995 | Hollstien et al. | |
| 5,454,811 A | 10/1995 | Huebner | |
| 5,482,411 A | 1/1996 | McGlasson | |
| 5,533,842 A | 7/1996 | Johnson et al. | |
| 5,538,423 A | 7/1996 | Coss et al. | |
| 5,554,154 A | 9/1996 | Rosenberg | |
| 5,569,254 A | 10/1996 | Carlson et al. | |
| 5,575,793 A | 11/1996 | Carls et al. | |
| 5,599,142 A | 2/1997 | Fujimoto et al. | |
| 5,613,810 A | 3/1997 | Bureller | |
| 5,653,712 A | 8/1997 | Stern | |
| 5,658,292 A | 8/1997 | Axelson, Jr. | |
| 5,667,509 A | 9/1997 | Westin | |
| 5,669,915 A | 9/1997 | Caspar et al. | |
| 5,697,158 A | 12/1997 | Klinzing et al. | |
| 5,725,530 A | 3/1998 | Popken | |
| 5,755,537 A | 5/1998 | Lubbering | |
| 5,755,721 A | 5/1998 | Hearn | |
| 5,810,821 A | 9/1998 | Vandewalle | |
| 5,810,828 A | 9/1998 | Lightman et al. | |
| 5,833,404 A | 11/1998 | Johnson et al. | |
| 5,856,922 A | 1/1999 | Jehanno | |
| 5,875,920 A | 3/1999 | Parent | |
| 5,890,897 A | 4/1999 | Kruger et al. | |
| 5,894,095 A | 4/1999 | DeMali | |
| 5,895,389 A | 4/1999 | Schenk et al. | |
| 5,941,706 A | 8/1999 | Ura | |
| 5,961,257 A | 10/1999 | Bettini et al. | |
| 5,980,248 A | 11/1999 | Kusakabe et al. | |
| 5,993,453 A | 11/1999 | Bullara et al. | |
| 5,993,454 A | 11/1999 | Longo | |
| 5,997,541 A | 12/1999 | Schenk | |
| 6,001,115 A | 12/1999 | Ahola et al. | |
| 6,022,352 A | 2/2000 | Vandewalle | |
| 6,022,356 A | 2/2000 | Noyes et al. | |
| 6,033,409 A | 3/2000 | Allotta | |
| 6,096,042 A | 8/2000 | Herbert | |
| 6,096,051 A | 8/2000 | Kortenbach et al. | |
| 6,110,174 A | 8/2000 | Nichter | |
| 6,146,385 A | 11/2000 | Torrie et al. | |
| 6,171,312 B1 | 1/2001 | Beaty | |
| 6,209,886 B1 | 4/2001 | Estes et al. | |
| 6,238,400 B1 | 5/2001 | Bays | |
| 6,277,135 B1 | 8/2001 | Wang | |
| 6,302,406 B1 | 10/2001 | Ventura | |
| 6,337,142 B2 | 1/2002 | Harder et al. | |
| 6,342,057 B1 | 1/2002 | Brace et al. | |
| 6,378,626 B1 | 4/2002 | Wallace | |
| 6,379,364 B1 | 4/2002 | Brace et al. | |
| 6,391,016 B2 | 5/2002 | Bays | |
| 6,416,517 B2 | 7/2002 | Harder et al. | |
| 6,436,103 B1 | 8/2002 | Suddaby | |
| 6,473,962 B1 | 11/2002 | Beduhn | |
| 6,484,814 B2 | 11/2002 | Bongers-Ambrosius | |
| 6,514,018 B2 | 2/2003 | Martinez et al. | |
| 6,527,778 B2 | 3/2003 | Athanasiou et al. | |
| 6,536,536 B1 | 3/2003 | Gass et al. | |
| 6,547,562 B2 | 4/2003 | Kumar | |
| 6,565,293 B2 | 5/2003 | Desmoulins | |
| 6,605,092 B2 | 8/2003 | Grumberg et al. | |
| 6,610,067 B2 | 8/2003 | Tallarida et al. | |
| 6,635,060 B2 | 10/2003 | Hanson et al. | |
| 6,645,227 B2 | 11/2003 | Fallin et al. | |
| 6,665,948 B1 | 12/2003 | Kozin et al. | |
| 6,702,531 B2 | 3/2004 | Linderholm | |
| 6,702,818 B2 | 3/2004 | Kupferschmid et al. | |
| 6,758,642 B2 | 7/2004 | Linderholm et al. | |
| 6,776,562 B2 | 8/2004 | Morrison et al. | |
| 6,783,532 B2 | 8/2004 | Steiner et al. | |
| 6,786,683 B2 | 9/2004 | Schaer et al. | |
| 6,849,071 B2 | 2/2005 | Whitman et al. | |
| 6,872,036 B2 | 3/2005 | Linderholm | |
| 6,874,980 B1 | 4/2005 | Noelle et al. | |
| 6,925,725 B2 | 8/2005 | Herrmann et al. | |
| 6,951,562 B2 | 10/2005 | Zwirnmann | |
| 6,974,481 B1 | 12/2005 | Carson | |
| 7,004,943 B2 | 2/2006 | Ferrante et al. | |

(56) References Cited

U.S. PATENT DOCUMENTS

| | | | |
|---|---|---|---|
| 7,011,661 B2 | 3/2006 | Riedel et al. |
| 7,021,933 B2 | 4/2006 | Caldwell |
| 7,033,363 B2 | 4/2006 | Powell |
| 7,048,477 B2 | 5/2006 | Abrams |
| 7,066,940 B2 | 6/2006 | Riedel et al. |
| 7,073,989 B2 | 7/2006 | Erickson et al. |
| 7,081,119 B2 | 7/2006 | Stihl |
| 7,094,242 B2 | 8/2006 | Ralph et al. |
| 7,108,459 B1 | 9/2006 | Mueller |
| 7,111,411 B2 | 9/2006 | Knopfle et al. |
| 7,121,773 B2 | 10/2006 | Mikiya et al. |
| 7,150,751 B2 | 12/2006 | Lechot |
| 7,163,542 B2 | 1/2007 | Ryan |
| 7,179,259 B1 | 2/2007 | Gibbs |
| 7,188,431 B2 | 3/2007 | Herrmann et al. |
| 7,210,881 B2 | 5/2007 | Greenberg |
| 7,226,450 B2 | 6/2007 | Athanasiou et al. |
| 7,235,940 B2 | 6/2007 | Bosch et al. |
| 7,258,692 B2 | 8/2007 | Thelen et al. |
| 7,303,363 B2 | 12/2007 | Krause et al. |
| 7,331,406 B2 | 2/2008 | Wottreng, Jr. et al. |
| 7,497,860 B2 | 3/2009 | Carusillo et al. |
| D593,389 S | 6/2009 | Clayton |
| 7,578,642 B2 | 8/2009 | Fritsche et al. |
| 7,641,000 B2 | 1/2010 | Albert |
| 7,670,328 B2 | 3/2010 | Miller |
| 7,681,659 B2 | 3/2010 | Zhang et al. |
| 8,167,518 B2 | 5/2012 | Mathis et al. |
| 8,394,099 B2 | 3/2013 | Patwardhan |
| 8,444,647 B2 | 5/2013 | Walen et al. |
| 8,511,945 B2 | 8/2013 | Apkarian et al. |
| 8,529,567 B2 | 9/2013 | Garcia et al. |
| 8,562,635 B2 | 10/2013 | Tanner et al. |
| 8,821,493 B2 | 9/2014 | Anderson |
| 8,894,654 B2 * | 11/2014 | Anderson ............. B25B 21/002 |
| | | | 173/176 |
| 9,204,885 B2 | 12/2015 | McGinley et al. |
| 9,526,511 B2 | 12/2016 | Anderson |
| 9,877,734 B2 | 1/2018 | Anderson |
| 10,245,043 B2 | 4/2019 | Xie |
| 10,736,643 B2 * | 8/2020 | Anderson ................. G01L 3/08 |
| 11,517,324 B2 | 12/2022 | Anderson |
| 11,839,385 B2 * | 12/2023 | Anderson ................. G01L 3/08 |
| 2001/0016744 A1 | 8/2001 | Kupferschmid et al. |
| 2001/0047219 A1 | 11/2001 | Oden |
| 2002/0038124 A1 | 3/2002 | Lee |
| 2003/0049082 A1 | 3/2003 | Morrison et al. |
| 2003/0143042 A1 | 7/2003 | Doyle et al. |
| 2003/0229354 A1 | 12/2003 | Schmieding et al. |
| 2003/0233098 A1 | 12/2003 | Markworth |
| 2004/0049128 A1 | 3/2004 | Miller et al. |
| 2004/0059317 A1 | 3/2004 | Hermann |
| 2004/0146367 A1 | 7/2004 | Gerhardt et al. |
| 2004/0179829 A1 | 9/2004 | Phillips et al. |
| 2004/0179910 A1 | 9/2004 | Theising et al. |
| 2004/0193173 A1 | 9/2004 | Knopfle et al. |
| 2004/0215395 A1 | 10/2004 | Strasser et al. |
| 2004/0265082 A1 | 12/2004 | Abrams |
| 2005/0116673 A1 | 6/2005 | Carl et al. |
| 2005/0131415 A1 | 6/2005 | Hearn et al. |
| 2005/0169717 A1 | 8/2005 | Field |
| 2005/0171504 A1 | 8/2005 | Miller |
| 2005/0171553 A1 | 8/2005 | Schwarz et al. |
| 2005/0192585 A1 | 9/2005 | Simmons |
| 2005/0261693 A1 | 11/2005 | Miller et al. |
| 2006/0085005 A1 | 4/2006 | Kenealy et al. |
| 2006/0096767 A1 | 5/2006 | Miller |
| 2006/0104731 A1 | 5/2006 | Etter et al. |
| 2006/0106363 A1 | 5/2006 | Aravena et al. |
| 2006/0217729 A1 | 9/2006 | Eskridge et al. |
| 2006/0224161 A1 | 10/2006 | Bhattacharyya |
| 2006/0241628 A1 | 10/2006 | Parak |
| 2006/0269372 A1 | 11/2006 | Goshima |
| 2007/0135803 A1 | 6/2007 | Belson |
| 2007/0217879 A1 | 9/2007 | Larsson |
| 2008/0027449 A1 | 1/2008 | Gundlapalli et al. |
| 2008/0077149 A1 | 3/2008 | Hoegerle |
| 2008/0119860 A1 | 5/2008 | McCarthy |
| 2008/0245159 A1 | 10/2008 | Garshelis et al. |
| 2008/0269755 A1 | 10/2008 | Malackowski et al. |
| 2009/0093830 A1 | 4/2009 | Miller |
| 2009/0162158 A1 | 6/2009 | Glodowski et al. |
| 2009/0196696 A1 | 8/2009 | Otsuka et al. |
| 2009/0245956 A1 | 10/2009 | Apkarian et al. |
| 2009/0297284 A1 | 12/2009 | Brown et al. |
| 2009/0326537 A1 | 12/2009 | Anderson |
| 2010/0114288 A1 | 5/2010 | Haller et al. |
| 2010/0160924 A1 | 6/2010 | Soliman |
| 2011/0245833 A1 | 10/2011 | Anderson |
| 2011/0301611 A1 | 12/2011 | Garcia et al. |
| 2012/0059378 A1 | 3/2012 | Farrell |
| 2012/0123418 A1 | 5/2012 | Giurgi et al. |
| 2013/0096561 A1 | 4/2013 | Miller et al. |
| 2013/0110117 A1 | 5/2013 | Soliman |
| 2013/0165937 A1 | 6/2013 | Patwardhan |
| 2014/0054053 A1 * | 2/2014 | Saito ..................... B23Q 5/326 |
| | | | 173/1 |
| 2014/0371752 A1 | 12/2014 | Anderson |
| 2015/0080966 A1 | 3/2015 | Anderson |
| 2015/0257808 A1 | 9/2015 | Sweeney |
| 2017/0231644 A1 | 8/2017 | Anderson |
| 2018/0140308 A1 | 5/2018 | Anderson |
| 2019/0013830 A1 | 1/2019 | Hoglund et al. |
| 2019/0029697 A1 | 1/2019 | Anderson et al. |
| 2019/0247057 A1 | 8/2019 | Anderson |
| 2020/0060694 A1 | 2/2020 | Anderson |

FOREIGN PATENT DOCUMENTS

| | | | |
|---|---|---|---|
| EP | 2392269 A1 | 12/2011 |
| JP | 59-196105 A | 11/1984 |
| JP | 2000516109 A | 12/2000 |
| WO | 1997024991 A1 | 7/1997 |
| WO | 1998018390 A1 | 5/1998 |
| WO | 2003101322 A1 | 12/2003 |
| WO | 2004019785 A2 | 3/2004 |
| WO | 2009158115 A1 | 12/2009 |
| WO | 2015006296 A1 | 1/2015 |

OTHER PUBLICATIONS

Mínguez, "The Work-Energy Theorem and the First Law of Thermodynamics," International Journal of Mechanical Engineering Education. 33(1):77-82 (2005) DOI:10.7227/IJMEE.33.1.8.

US: Final Office Action in U.S. Appl. No. 18/828,790 dated Feb. 10, 2025 (15 pages).

US: Non-Final Office Action in U.S. Appl. No. 18/828,756 dated Nov. 1, 2024 (32 pages).

US: Non-Final Office Action in U.S. Appl. No. 18/828,790 dated Nov. 1, 2024 (33 pages).

US: Notice of Allowance in U.S. Appl. No. 18/073,640 dated Jun. 21, 2024 (8 pages).

US: Notice of Allowance in U.S. Appl. No. 18/828,756 dated Feb. 20, 2025 (12 pages).

AU: Notice of Acceptance dated Mar. 13, 2025 in Australian Patent Application No. 2023208149 (3 pages).

US: Notice of Allowance in U.S. Appl. No. 18/828,790 dates Apr. 21, 2025 (7 pages).

* cited by examiner

Force produced by torque

77

78

$T_d$

61

82

DRIVING DEVICES AND METHODS FOR DETERMINING MATERIAL STRENGTH IN REAL-TIME

CROSS-REFERENCE TO PRIORITY APPLICATION

This application is a continuation of U.S. application Ser. No. 16/915,063, filed Jun. 28, 2020, and entitled, "DRIVING DEVICES AND METHODS FOR DETERMINING MATERIAL STRENGTH IN REAL-TIME," which is a divisional of U.S. application Ser. No. 16/077,021, filed on Aug. 9, 2018, and entitled "DRIVING DEVICES AND METHODS FOR DETERMINING MATERIAL STRENGTH IN REAL-TIME," which claims priority to International PCT Application No. PCT/US17/17517, filed Feb. 10, 2017, entitled "DRIVING DEVICES AND METHODS FOR DETERMINING MATERIAL STRENGTH IN REAL-TIME," which claims priority to U.S. Provisional Application No. 62/294,717, filed Feb. 12, 2016, entitled "Driving Devices and Methods for Determining Material Strength in Real-Time," the entire contents of which are hereby incorporated by reference herein in their entirety.

BACKGROUND

Torque wrenches are used to measure the torque applied to a screw or other implant, particularly when the situation calls for calibration of the placement of a mechanical construct. Empirical data can guide an operator on the optimal torque or tightness to place a screw into material when an operator knows the strength of the screw and the material into which it is to be inserted. Optimizing the strength of the mechanical construct is done to prevent construct failure. In reality, there can be many situations where some of these data are missing. For example, when placing screws into materials that have a range of strengths, such as wood, concrete, and bone, etc. Unfortunately, in these situations the required torque to place a screw or other implant is often unknown.

In the case of human or animal bone, different bones have different strengths, thicknesses and layers. A femur is different than a metacarpal bone. In addition, bone can be affected by age, disease, and metabolic conditions such as osteoporosis. People with osteoporosis often require palliative surgery for fractures, joint replacements, or spine surgery. Implantable hardware intended for patients with normal bone strength can fail in people with osteoporosis. Less than 10% of patients undergoing orthopedic, spine and/or neurosurgery have had a study to delineate their bone density/strength. Even if a test has been performed, such as a Dexa scan, the region being operated on may not have been the subject of the test. For example, the Dexa scan may show osteoporosis in the lumbar spine, which is not helpful if the operative site is the hip or the tibia.

During any procedure where a drill or other driver is used to advance a tool into and through bone, the user must consciously and carefully limit the penetration to the desired depth. If the user allows the tool to penetrate further, the patient can suffer injury to distal structures such as nerve, brain, spinal cord, artery, vein, muscle, fascia, bone or joint space structures. These types of injuries can lead to severe patient morbidity and even death. The devices inserted to a drilled bore often must fit within a narrow length range that can vary sometimes by no more than a millimeter or less.

Once the drilling of a bone is safely complete, it is often prudent to obtain the depth of the bore made by the drilling tool. Many procedures require knowledge of the depth of tool penetration, such as in the placement of internal fixation devices, screws and other implantable hardware. Selecting an appropriate length of the screw or other implant necessary for the procedure depends upon such knowledge of the bore's depth. Conventional techniques used in the art are often inconvenient, time consuming and unreliable often requiring trial and error and multiple exposures to radiographs before the proper implant insertion is achieved.

A common way to obtain the depth of the bore formed by a drilling tool is to use a depth gauge. Often users must interrupt the drilling procedure in order to palpate or measure with a depth gauge whether or not the desired depth has been achieved. In many instances a user will take a radiograph during a drilling procedure to confirm the appropriate depth of penetration has been achieved or take a radiograph while the depth gauge is in place to ensure the information the gauge provides is accurate. Depth gauges used in the art can be inaccurate resulting in a user placing a screw of an inappropriate length not often identified until a confirming radiograph is taken. Each radiograph taken increases the radiation exposure of the surgeon, staff and patient in the operating suite. Depth gauges known in the art can also break and require the user to retrieve it from the bore. Inconvenient and inaccurate depth measurement devices and methods can result in improperly sized screws that must be removed and replaced with new properly sized screws. Wasted hardware, increased disruptions and delays in orthopedic procedures ultimately increase the expense of a procedure as well as expose the surgeon, staff and the patient to unnecessary radiation. The cost of the additional time, the wasted hardware and the radiation exposure are quite significant.

SUMMARY

In one aspect, disclosed is a system including an instrument having a working tool configured to penetrate a tissue; a sensor configured to generate in real-time one or more torque signals related to torque of the working tool; a controller in operative communication with the sensor and configured to receive the one or more torque signals. The controller processes the torque signals into one or more processed signals representative of torque, energy, power or a combination thereof. The system also includes a display providing to the user in real-time the one or more processed signals.

The controller can be configured to determine, based at least on the energy, a regional material strength of the tissue. The one or more torque signals can be representative of a regional material strength of the tissue. The system can further include one or more motors housed in a body of the instrument. The one or more motors can include a rotational drive motor having a drive shaft. The rotational drive motor and drive shaft can be part of a motor sub-assembly comprising the sensor and a motor mount. The motor mount can be coupled to a back end of the body. The rotational drive motor shaft can be coupled to a bearing at a front end of the body and the sensor can be positioned between the rotational drive motor and the motor mount such that the sensor does not contact the body directly. The motor sub-assembly can be suspended between the bearing and the motor mount coupled to a back end of the body.

The system can further include an axial drive motor. The body can further include one or more guides operatively coupled to the axial drive motor. The one or more guides can include a guide harp having a distal guide element configured to receive the working tool therethrough. Withdrawal of the guide harp by the axial drive motor in a proximal direction can effect extension of the working tool relative to a distal end of the distal guide element. The guide harp and axial drive motor can be configured to achieve real-time depth control and measurement of the working tool penetration. The system can further include a removable drill sleeve attached to an end of the distal guide element. The one or more guides can include more than one guide coupled to the instrument and symmetrically disposed around a longitudinal axis of the working tool. The guide harp can include one or more rods providing support to bear a load of the instrument. The one or more rods can be telescoping rods providing the instrument with a range in penetration lengths. The one or more rods can exit through a back end of the body. The one or more rods can be coupled to the body of the instrument by a front guide having a slip bushing through which the one or more rods of the guide harp extend. The one or more rods of the guide harp can additionally be coupled to the body of the instrument near a back end of the body by extending through a rear guide. The rear guide can be a housing for a harp feed guide sub-assembly. The harp feed guide sub-assembly can be configured to engage the one or more rods. The one or more rods can include threads or step gear cuts on at least a portion of a length of the one or more rods configured to engage corresponding features within the harp feed drive sub-assembly of the rear guide.

The system can include one or more axial force sensors. The one or more axial force sensors can sense a force on at least one of the guide harp and the working tool. The system can include a first axial force sensor configured to measure a force applied to the guide harp and a second axial force sensor configured to measure a force applied to the working tool. The display can provide in real-time information from the one or more axial force sensors. The sensor can be configured to measure in real-time torque of the working tool in the x-axis, the y-axis, and the z-axis, simultaneously. The display can provide the torque in the x-axis, the y-axis, and the z-axis to a user. The display can provide to the user a rise in slope on any one of the x-axis, the y-axis, or the z-axis.

The sensor can be a torque sensor or a force sensor. The working tool can be a drill bit, a saw, a burr, a reamer, a cutting element, a driving element, or a self-drilling implant. The one or more motors can include one or a combination of rotational drive motors, a non-electric drive motor, pneumatic motors or actuators powered by a gas source, electrical motors, hydraulic actuators, hand-powered cranks. The controller can be in operative communication with the one or more motors.

In an interrelated aspect, provided is a method including penetrating a tissue with a working tool of an instrument; using a sensor on the instrument to generate in real-time one or more signals related to torque of the working tool; communicating the one or more torque signals from the sensor to a controller; processing the one or more torque signals received into one or more processed signals representative of torque, energy, power, or a combination of torque, energy, and power; and displaying the one or more processed signals to a user.

The method can further include determining, based at least on the energy, a regional material strength of the tissue. The one or more torque signals can be representative of a regional material strength of the tissue. The instrument can further include one or more motors housed in a body of the instrument and driving the working tool to penetrate the tissue by a rotational drive motor having a drive shaft. The rotational drive motor and drive shaft can be part of a motor sub-assembly having the sensor and a motor mount. The method can further include suspending the motor sub-assembly between a bearing at a front end of the body and the motor mount coupled to a rear end of the body such that the sensor is positioned between the rotational drive motor and the motor mount and does not contact the body directly. The method can further include transforming the one or more torque signals received from the sensor by the controller into energy using the work-energy theorem. The method can further include providing on a display information relating to the regional material strength of the tissue. The regional material strength of the tissue can provide information regarding whether the tissue is osteoporotic. The method can further include creating a pilot hole in the tissue with the working tool.

The method can further include providing real-time depth control to mitigate inadvertent plunge of the working tool based on the one or more processed signals displayed to the user. An axial drive motor can be operatively coupled to one or more guides. The one or more guides can include a guide harp having a distal guide element configured to receive the working tool therethrough. The method can further include using the axial drive motor to withdraw in a proximal direction the distal guide element revealing a length of the working tool extending beyond a distal engagement end of the instrument. The method can further include measuring in real-time a depth of the working tool into the tissue based on a distance of proximal withdrawal of the distal guide element.

The method can further include using one or more axial force sensors to sense a force on at least one of the guide harp and the working tool. The real-time data from the one or more axial force sensors can be displayed to a user. The method can further using a first axial force sensor to measure a force applied to the guide harp and using a second axial force sensor to measure a force applied to the working tool. Penetrating a tissue can include penetrating a joint, a pedicle sidewall, a pelvic brim, or a cranium, and the method is performed without fluoroscopy. Using a sensor to generate signals related to torque of the working tool can include sensing torque in the x-axis, the y-axis, and the z-axis, simultaneously and in real-time. The torque in the x-axis, the y-axis, and the z-axis can be displayed and the method can further include detecting a rise in slope on any one of the x-axis, the y-axis, or the z-axis. An angle of the working tool can be redirected while penetrating the tissue based on the detected rise in slope. The sensor can be a torque sensor or a force sensor and the working tool can be a drill bit, a saw, a burr, a reamer, a cutting element, a driving element, or a self-drilling implant.

In an interrelated aspect, described is an instrument having one or more motors housed in a body of an instrument, at least one of the one or more motors configured to drive a working tool to penetrate a tissue; a guide harp coupled to the body of the instrument and having a distal guide element having a central channel configured to receive the working tool therethrough; a first sensor configured to measure in real-time a force of the working tool along a longitudinal axis of the working tool; a second sensor configured to measure in real-time a force against the distal guide element; and a controller in operative communication with the one or more motors, the first sensor and the second sensor.

The first sensor and the second sensor can be axial force sensors. The one or more motors can include a rotational drive motor having a drive shaft configured to extend through a bushing within a forward end of the body. The first sensor can be an axial force sensor incorporated within the bushing such that a force applied on the working tool along the longitudinal axis is sensed. The second sensor can be an axial force sensor positioned in a rear end of the body such that a force applied on the guide harp along the longitudinal axis is sensed. The instrument can further include an output configured to provide information from at least one of the first and second sensors. The output can provide alerts regarding an amount of force on the guide harp, an amount of force on the working tool, or both. The instrument can further include a third sensor configured to generate in real-time one or more signals related to torque of the working tool. The controller can be in operative communication with the third sensor and configured to receive the one or more torque signals. The controller can process the torque signals into one or more processed signals representative of torque, energy, power, or a combination of torque, energy, and power. The controller can be configured to determine, based at least on the energy, a regional material strength of the tissue. The one or more torque signals can be representative of a regional material strength of the tissue.

In an interrelated aspect, disclosed is a method of determining a regional material strength of a tissue using a surgical instrument. The method includes penetrating a tissue with a working tool of an instrument; using a sensor on the instrument to generate in real-time one or more signals related to torque of the working tool; communicating the one or more torque signals from the sensor to a controller of the instrument; processing the torque signals into one or more processed signals representative of energy; and displaying the one or more processed signals as accumulated energy. The accumulated energy is displayed as a function of position or as a function of time.

In an interrelated aspect, disclosed is a method of preventing inadvertent plunge using a surgical instrument. The method includes penetrating a tissue with a working tool of an instrument; using a sensor on the instrument to generate in real-time one or more signals related to torque of the working tool; communicating the torque signals from the sensor to a controller; processing the received torque signals into one or more processed signals representative of power; and graphically displaying the one or more processed signals as power.

Graphically displaying the one or more processed signals as power can include plotting power as a function of time or as a function of depth. The method can further include stopping the penetration upon sensing a drop in power. Stopping the penetration can include the controller stopping the motor housed in a body of the instrument. The motor can be a rotational drive motor operatively coupled to the working tool. The instrument can further include an axial drive motor operatively coupled to one or more guides. The one or more guides can include a guide harp having a distal guide element configured to receive the working tool therethrough. The axial drive motor can be configured to withdraw in a proximal direction the distal guide element revealing a length of the working tool extending beyond a distal engagement end of the instrument. Stopping the penetration can include preventing proximal withdrawal of a guide harp by the axial drive motor. The method can further include communicating the one or more processed signals to an external electronic device. The signals can be communicated wirelessly. Graphically displaying the one or more processed signals can include graphically displaying on the external electronic device.

In an interrelated aspect, disclosed is a system for preventing inadvertent plunge using a surgical instrument. The system includes a working tool configured to penetrate a tissue; a sensor configured to generate in real-time one or more signals related to torque while the working tool penetrates the tissue; and a controller in operative communication with the sensor and configured to process the received torque signals into one or more process signals representative of torque, energy, power, or a combination of torque, energy, and power.

The system can include an output providing the one or more processed signals. The output can be a graphical user interface. The graphical user interface can be on an external computing device in communication with the system. The external computing device can be in wireless communication with the system. The graphical user interface can be configured to display the one or more processed signals as a plot of power as a function of time or as a function of depth. The one or more processed signals provided on the output can provide information to the user regarding penetration of the working tool and when to stop penetration of the working tool. A drop in power can signal when to stop penetration of the working tool. The one or more processed signals provided on the output can include accumulated energy, wherein the accumulated energy provides information to a user regarding material strength of the tissue.

Other features and advantages will be apparent from the following description of various embodiments, which illustrate, by way of example, the principles of the disclosed devices and methods.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

Figure 1A:
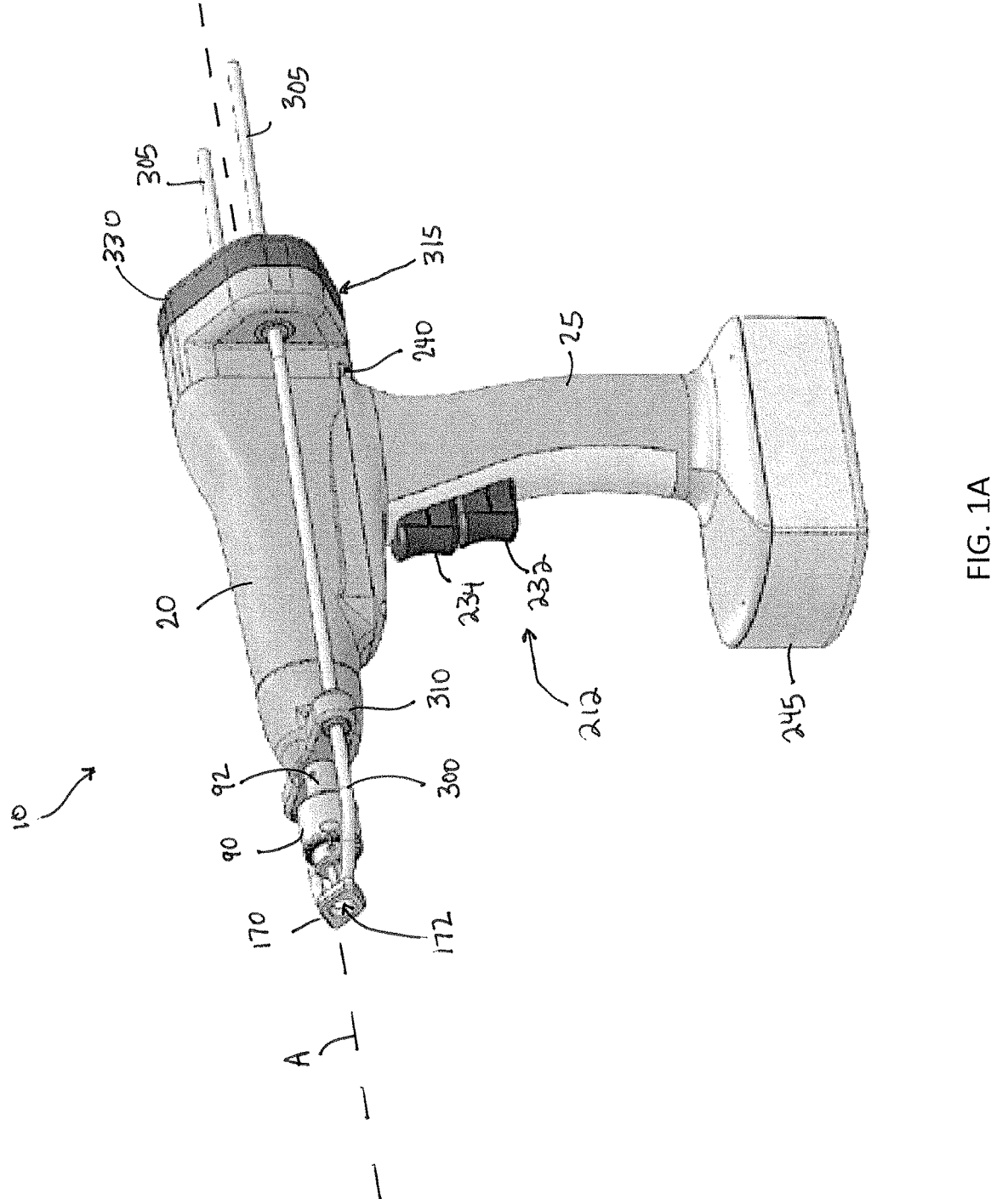
FIGS. 1A, 1B, and 1C illustrate perspective, side and top views, respectively, of one implementation of an instrument.
Figure 1B:
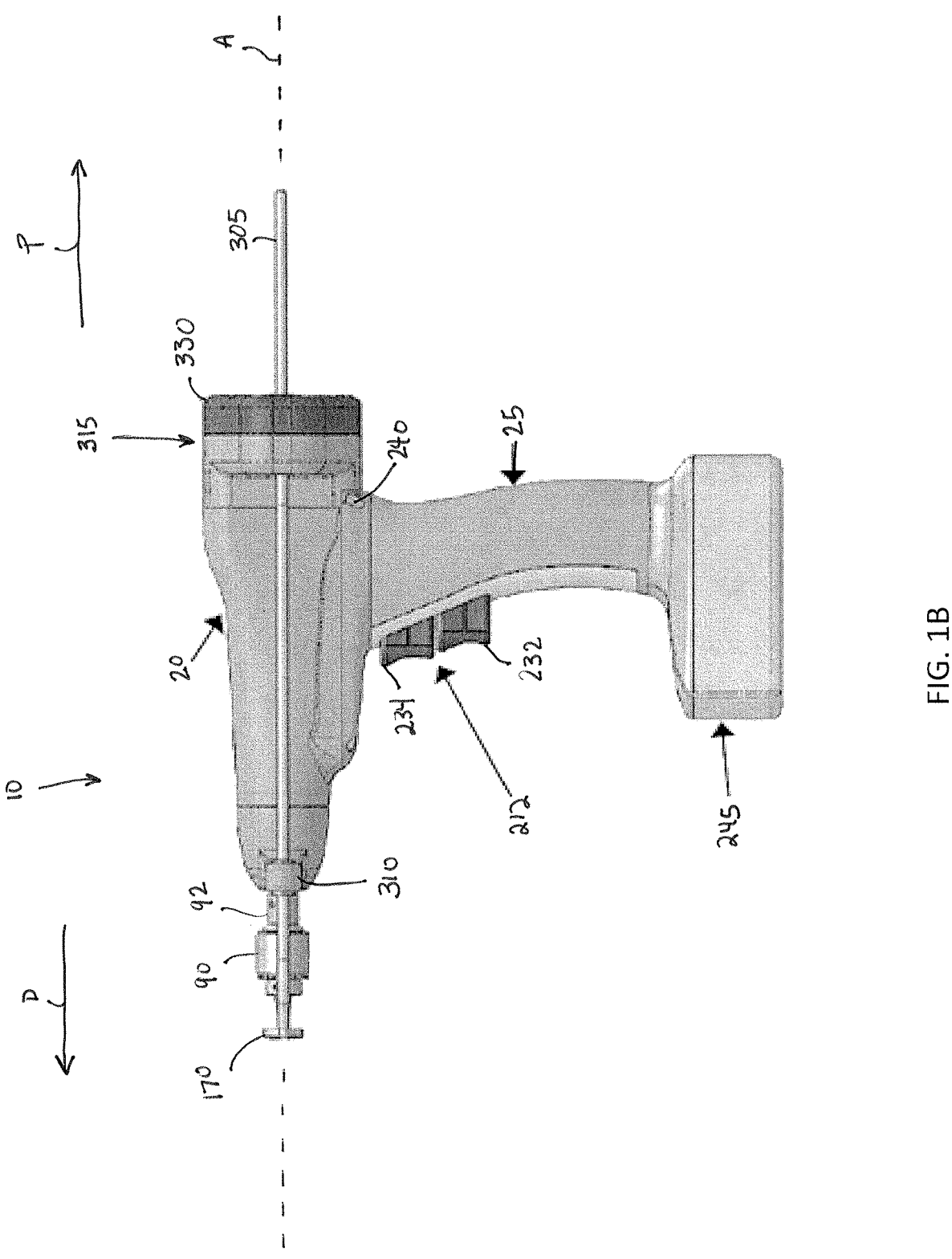
Figure 1C:
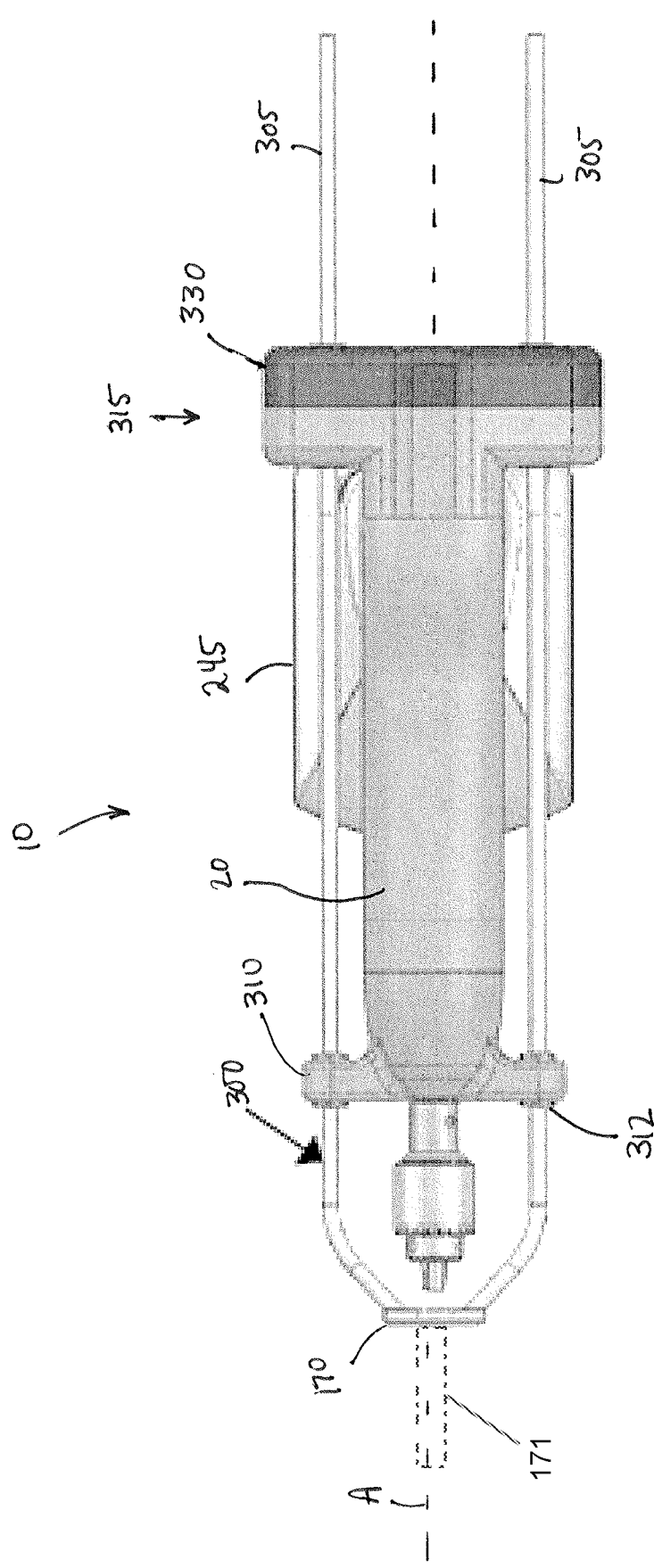

It should be appreciated that the drawings herein are exemplary only and are not meant to be to scale.

DETAILED DESCRIPTION

The present disclosure relates generally to instruments for preparing a bore, cutting, and/or driving an implant into a material such as animal tissue.

The devices, systems and methods described herein provide for the measurement of working tool torque, power, and energy essentially free from motor and gearbox noise. Torque and power can provide for instantaneous snapshot data, which can be provided to a user for the quick decision-making on depth, plunge prevention and skive prevention. Furthermore, provided is a system configured to correlate drilling energy to pullout strength. The energy data can be a cumulative number and therefore can give the overall "story" versus a simple snapshot. The energy data obtained by the devices, systems described herein can also be evaluated by an algorithm based upon drilling energy, drill hole depth and drill bit type and size to determine regional bone density and strength in real-time that correlate empirically with failure testing values. Knowing pullout strength and bone density can allow for the estimation of potential construct strength to help surgeons select the proper implants to use, for example, locking or non-locking plates and/or screw.

As used herein, "drilling energy" includes the energy it takes for the instrument (i.e. instruments described herein when used as a drill) to drill a hole into a bone. As used herein, "screw insertion energy" includes the energy it takes for the instrument (i.e. instruments described herein when used as a screw driver) to screw the screw into a pre-drilled hole. Also as used herein, "pullout strength" is the peak force (referred herein also as maximum force) on the force vs. time curve when pulling a screw placed into that hole out with a motorized test stand "Mark-10 ESM301 Motorized Test Stand with a Mark-10 Series 5 M5-005 Force Meter."

The devices described herein also provide real-time depth control and eliminate inadvertent "plunge" past the far cortex. The devices described herein also provide real-time depth measurement integrally related to its depth control that provides significantly more accurate readings that are less time-consuming. The devices described herein can also detect impending cortical and joint penetration at varied skive angles, for example, when penetrating a joint, pedicle sidewall, pelvic brim, or cranium, especially those that are osteoporotic, without the routine use of fluoroscopy, by sensing and displaying drilling torque, not only in the z (linear or axial) axis, but also in the x and y axes (x-y plane), in real-time. The devices described herein provide true 3D awareness as the rise in the slope can be detected on any axis whereas fluoroscopy only detects pending penetration in one plane. The devices described herein provide for the torque and/or power curves to rise at angles that correlate with the angles at which the instrument contacts and penetrates the denser cortex allowing the surgeon time to redirect the working tool away from that cortex keeping the tool endosteal, or down a canal like a pedicle all without radiation, guidance systems, preoperative CTs, robotic arms or other expensive and time-consuming technology. The devices described herein can incorporate an integrated GUI (graphical user interface) or a wireless GUI output. The devices described herein are portable, light-weight, and inexpensive to use and may lead to a reduction in the habitual fluoroscopy use during common screw and implant placements.

It should be appreciated that where the description is directed to a medical instrument, the concepts, features and/or components can be used for non-medical applications. Further, where the description is directed to a drilling device, it should be appreciated that other devices are considered herein including saws, reamers, burrs, and other material cutting or driving instruments.

The instrument described herein can include a working tool configured to cut a material, whether with a saw, drill bit, reamer, self-drilling screw, or other tool. The instrument can also be configured to include a working tool configured to drive hardware such as screws or wires into materials with or without a pre-drilled pilot hole. The instrument described herein can measure the energy that is expended by the tool to cut or the tool to drive. The torque of the working tool can be measured using a sensor including, but not limited to, a torque sensor or a force sensor. The sensor can be configured to measure in real-time torque of a working tool while the working tool penetrates the tissue and generate one or more torque signals. In some implementations, the instrument can include a torque sensor as a component of the motor mount. For example, the motor, torque sensor and gearbox can be coupled together and mounted onto the housing creating a floating assembly. For example, the torque sensor can be positioned between the motor and the motor mount and the entire motor sub-assembly suspended from front to back such that the motor sub-assembly is only in contact with the housing at the back end by the motor mount and at the front end by a bearing creating a floating motor assembly. In other implementations, the instrument can include a force sensor under a level arm connected to the motor mount. In further implementations, the instrument can include a torque sensor on a bushing allowing for the exit of the working tool or tool chuck from the tool body, as will be described in more detail below.

Previously, to select the proper implant for placing into a patient the surgeon would make a guess at the regional bone strength. Efforts have been made to quantify maximum insertion torque ("MIT") as a tool for estimating regional bone strength and construct strength, but MIT is not consistently useful in predicting construct viability and hardware failure because MIT does not consistently correlate with pullout strength of the hardware or other failure testing modalities. However, as described in more detail herein, transformation of insertion torque data into energy, for example, electronically using the work-energy theorem, does correlate with pullout strength. As will be described in more detail below, using a pilot hole/screw insertion model, the drilling energy of the working tool to make the pilot hole correlates directly with both regional material strength and with screw pullout strength.

Turning now to FIGS. 1A-1C, FIG. 2, and FIG. 5A, the instrument 10 can include a body 20 that houses two drive motors 30, 60, one or more guides such as a guide harp 300 having a distal guide element 170, and a working tool 110 such as a drill bit, saw, burr, reamer, or other cutting element or driving element such as a screw driver. A drill sleeve/guide or tool sleeve/guide (see item 171 in FIG. 1C) can attach to an end of distal guide element 170. The working tool 110 can be coupled via a chuck 90 to the instrument 10. The one or more guides can be coupled to the instrument 10 and symmetrically disposed around the longitudinal axis A of the working tool 110. The drive motor 60 rotates the chuck 90 and the working tool 110 around the longitudinal axis A of the working tool 110. The first drive motor 30 can be an axial drive motor, for example seated near the proximal end (rear) of the body 20, and the second drive motor 60 can be a rotational drive motor, for example seated near the distal (front) end of the body 20. The axial drive motor 30 can power the one or more guides to move in an axial direction either forward, for example, for zeroing, or backwards such that the distal tip of the working tool 110 extends beyond the distal engagement region in order to engage the work. Thus, extension of the working tool 110 relative to the distal engagement end of the instrument 10 can be effected by the movement of one or more guides on the instrument 10. It should be appreciated that the distal engagement end of the instrument can include a tool sleeve or guide.

Although the implementations shown herein use motors, such as a stepper motor powered by a battery, it should be appreciated that power systems other than rotational drive motors are considered. For example, a non-electric drive motor, pneumatic motors or actuators powered for example by a nitrogen gas source, electrical motors, hydraulic actuators, hand-powered cranks, and the like or a combination thereof can be incorporated into the instrument. It should also be appreciated that a motor and gearing can be used in place of the two-motor implementation.

As will be described in more detail below, the instrument 10 can instantaneously sense, meter and control the work created by the working tool 110. For example, the torque, power usage and/or the energy can be sensed, metered, and reported to the operator graphically and/or numerically and/or with gauges. Instantaneous sensing, metering and controlling the instrument 10 can help to prevent injury to surrounding tissues and structures that could otherwise be caused by the working tool. For example, sensing, metering and controlling the rotational speed of the drive can reduce the risk of heating surrounding tissue and bone, for example to the point of causing localized burns. Sensing, metering and controlling the axial motion and/or relative extension of the working tool can prevent penetrating injuries, for example, to structures distal of the target such as nerve, brain, spinal cord, artery, vein, muscle, fascia, bone or joint space structures. Instantaneous sensing, metering and controlling the bore created as the working tool penetrates the tissue can provide an advantage when selecting implants for insertion. For example, the length of the drilling hole and subsequently the length of the implant needed can be simultaneously metered upon creating the bore. This eliminates the need for an additional step of measuring the depth of the bore created with a separate device. Further, depth gauges can frequently provide false measurements resulting in users selecting the wrong size implant for insertion and requiring them to remove the implant and reinsert a different sized implant. Conventional depth gauges are also prone to breakage, which can lead to additional time usage and patient morbidity. Sensing, metering and controlling the depth of the bore in real-time or as it is being created eliminates the trial-and-error process of selecting the correct implant for the procedure, which ultimately can improve patient safety and save operating time, cost and the need for additional procedures like repeated radiographs in determining implant size.

Features of the instruments described herein are related to those described in U.S. Pat. Nos. 8,821,493 and 8,894,654, which are each incorporated by reference herein in their entireties.

Instrument Guides

Again with respect to FIG. 1A, the one or more guides of the instrument 10 can include a guide harp 300 that can be withdrawn in a proximal direction to reveal a length of the working tool 110 extending beyond the distal engagement end of the instrument 10. The guide harp 300 can include two or more supporting arms or rods 305 positioned symmetrically around the central, longitudinal axis A of the working tool 110. The symmetrical orientation of the guide harp 300 around the central longitudinal axis A that is coaxial with the direction of force applied by the working tool 110 prevents the guide from acting like a lever arm. It should be appreciated that the harp 300 can be designed to incorporate one arm. In this implementation, a distal part of the arm can bend towards and surround the working tool, which would allow the working tool to act as a functional support arm to stabilize the construct from levering or moving off of the longitudinal axis. The axis of the guide harp 300 is aligned with the axis of the working tool 110 which is aligned with the direction of axial force being applied to increase stability of the instrument 10 and avoids the guide harp 300 from inadvertently causing pivoting movements away from the z-axis. The guide harp 300 can have one, two, three, or more rods 305 that provide support to bear the load. The rods 305 of the guide harp 300 can be singular units or can have telescoping rods. Telescoping rods can provide the instrument 10 with a larger range in overall penetration length in a more efficient configuration and eliminate the rods 305 from exiting the back end of the drill. The telescoping rods can each include an actuator such as a pneumatic, hydraulic, motorized or other actuator that causes the guide harp 300 to telescope and change overall guide length (i.e. telescope outward to lengthen or telescope inward to shorten). In another implementation, the telescoping guide harp 300 can be used to achieve depth control without the use of the axial drive motor 30. For example, the axial drive motor 30 can be replaced by a hydraulic or pneumatic motor, as can the rotational motor.

The rods 305 of the guide harp 300 can be coupled to the body 20 of the instrument 10 such as via a front guide 310 having a slip bushing 312 through which the rods 305 of the guide harp 300 extend. The rods 305 of the guide harp 300 can also couple to the body 20 of the instrument 10 near a proximal end of the body 20 by extending through a rear guide 315. Within the rear guide 315 can be a housing for a harp feed guide sub-assembly 325 (see FIG. 3). The harp feed guide sub-assembly 325 is configured to engage the rods 305. For example, the rods 305 can include threads or simple step gear cuts on at least a portion of their length configured to engage with corresponding features within the harp feed drive sub-assembly 325 of the rear guide 315, including threads or a pinion of a rack and pinion system and which will be described in more detail below. The rods 305 of the guide harp 300 can extend clear through the rear guide 315 such that the feed length of the guide harp 300 need not be enclosed within the body 20 and instead can extend out the rear housing cover 330 of the rear guide 315 (see FIGS. 1A-1C). This allows for the guide harp 300 to be virtually any length and size while preventing excess bulkiness of the body 20 in that the drill body 20 may only enclose the motors and gearing. In some implementations, the guide harp 300 having a longer length can include more than two rods 305, for example, three or four or more rods 305 disposed around the longitudinal axis A to improve rigidity and stability of the guide harp 300 and preventing too much flexibility. In another implementation, the rods may be telescoping such that they do not extend out of the rear housing cover 330.

As mentioned above, the guide harp 300 can be coupled at a forward end to a distal guide 170. As described above, the distal guide 170 can form the forward engagement end of the instrument or a drill sleeve/guide or tool sleeve/guide (item 171 in FIG. 1C) can attach to an end of distal guide element 170 such that the distal tool guide 171 forms the forward engagement end of the instrument. It should be appreciated that where the distal guide 170 is mentioned or described herein that the distal guide 170 can include a tool guide 171 or such as those described in U.S. Pat. No. 8,821,493, which is incorporated by reference herein. The distal guide 170 can include a central channel 172 through which the working tool 110 can extend to engage the work. The distal guide 170 can have a tapered geometry or reduced outer diameter such that its contact surface is relatively small compared to the distal end of the body 20 and the bulk of the instrument 10 is focused into a small area of contact with the work. This distal tapered geometry may take the form of a removable distal tool guide coupled to the distal guide 170. The distal guide 170 can also include gripping features at its forward surface such as spikes or other protrusions such that the guide 170 can hold its position on the work. The distal guide 170 and tool sleeve/guide 171 also can function as a tissue protector and/or tissue retractor, thus simplifying procedures using the instrument.

The distal guide 170 can assist in the engagement of bone, fracture plates or other implants or joint parts. One or more portions of the distal guide 170 can press onto or couple with the implant, for example by directly pressing or screwing the implant onto one or more corresponding features of the distal guide 170. The distal guide 170 can engage an implant, such as a fracture fixation plate, by a threaded interface, or by another mechanism, such that the guide 170 screws into, or otherwise couples with the implant. The guide 170 can be coupled to the implant in a generally perpendicular configuration. Alternatively, distal guide 170 can connect to the implant at an angle away from perpendicular. The guide 170 can include an interface that provides a unique connection with the implant. For example, the distal guide 170 can include a pin-index type connection or a diameter-index type system that provide non-interchangeable connections between the distal guide 170 and the implant. As such, a specific implant can interface with a particular distal guide 170 to prevent misconnections. The specific geometry of the interface between the distal guide 170 and the implant can vary. For example, the distal guide 170 can include one or more geometric features that extend from a forward surface of the distal guide 170 that couple with corresponding geometric features provided on the implant such that the two properly and uniquely interconnect. The corresponding geometric features can dictate the type of implant that can be used with a particular distal guide 170 providing for a unique pairing between the two.

Working Tools

As mentioned above, the working tool 110 can be connected to the instrument 10 using a rotatably-driven coupler or chuck 90 with or without a chuck extension 92. A drive shaft 62 of the rotational drive motor 60 can extend through a forward end of the body 20 and couple with the chuck 90 or chuck extension 92. The chuck 90 can be a conventional coupler such as a three jaw chuck in which the jaws grasp the proximal portion of the tool and hold it firmly in place. The chuck 90 can be actuated to open or close the jaws by a rotation mechanism or a key or other technique known in the art. The chuck 90 can also be a quick-release type of coupler. The chuck 90 can be accessed external of the body 20. This accessibility of the chuck 90 relative to the instrument 10 allows for a user to make reliable connections between the working tool and the chuck 90. The exterior access can also allow for shorter, safer driven tools than if the chuck 90 was internal to the instrument body 20. Additionally, the exterior access can provide for ease of cleaning this portion of the instrument 10.

The working tool 110 as described herein can include, but is not limited to, tools such as a drill bit, Kirschner (or other) wire, pin, trochar, burr, screwdriver, wrench, reamer, saw, saw blade, router, router bit, stepped drill bit, bone plug removal tools, bone harvesting tools, bone marrow harvesting tools, bone marrow aspirating tools or any other tools that can be reversibly attached to a chuck 90 or other type of coupling device. It should be appreciated that where a working tool 110 is described herein as a drill bit or wire or pin or other type of tool that such description is not intended to be limiting. It should be appreciated that a wide variety of tools can be used as the working tool with the instruments described herein. For example, the working tool can be a saw blade connected to a coupler that oscillates or reciprocates the saw blade or a wire driver.

The working tool 110 can be made of metal materials such as titanium metal or stainless steel that can be sterilized and reused. Alternatively, the working 110 can be made of polymeric material that can be discarded after each use. The material can be chosen to provide the necessary strength to allow the proper tool action.

Tool Actuation

Actuation of the drive motors 30, 60 and other features of the instruments described herein can vary. Actuators can include triggers, buttons and switches that can be retracted, pressed, squeezed, slid or otherwise actuated to perform a certain function of the instrument 10. The actuators can be incorporated into a handle of the instrument 10 in such a way that is ergonomically comfortable for a user. For example, the instrument can include a pistol grip handle having trigger-type actuators such that the instrument 10 can be easily and comfortably held and actuated during use. The pistol grip handle can include a lip under the actuators for the fingers to press against. It should be appreciated, however, that the instrument 10 can have other configurations such as a straight-bodied instrument that does not include a pistol grip handle.

Again with respect to FIGS. 1A-1C, each drive motor can have a separate actuator for activation. For example, the drive motor 30 can be turned on by actuator 234 and the drive motor 60 can be turned on by actuator 232 or vice versa. The actuators 234, 232 can be depressible triggers positioned on a handle 25 of the body 20, such as within a trigger housing 212. The actuators 234, 232 can adjust the speed of the drive motors 30, 60 in a manner that is proportional to the degree of depression of the actuators 234, 232, for example relative to the instrument handle 25. The direction motors moves can be changed from a forward to a reverse direction, for example, by the position of a switch or other selectable mechanism. Further, the motor can be biased in either rotational direction. Alternatively, the actuator 232 can be a forward trigger and actuator 234 can be a reverse trigger that can each actuate both drive motors 30, 60. The forward trigger 232 can be a two-stage forward trigger 232 such that it can engage the rotational drive motor 60 in the first stage (i.e. effecting working tool rotation) and the axial drive motor 30 in the second stage (i.e. effecting working tool extension). The speed of the rotational drive motor 60 can be proportional to the degree of actuation of the first stage of the forward trigger 232, for example depression of the trigger 232. The speed of the axial drive motor 30 can be proportional to the degree of actuation of the second stage of the forward trigger 232. In an implementation, the trigger 232 in the first stage can engage the rotational drive motor 60. The tool spins and with further depression of the trigger 232 can reach full speed. Just before the trigger 232 enters the second stage, the axial drive motor 30 can engage. In some implementations, the axial drive speed can be between about 0.25 mm/second to about 3 mm/second. In other implementations, the axial drive speed can be approximately 1 mm/second. The axial drive motor 30 can cause withdrawal of the guide harp 300 in a proximal direction P (see FIG. 1B) to reveal a length of the working tool 110 allowing it to engage with and bore into the work as the user applies pressure to the instrument 10 and keeps it engaged with the work. As will be discussed in more detail below, an axial force sensor can be incorporated that measures force applied to the guide harp 300, for example along the z-axis, that assists a user in keeping the instrument engaged with the work.

As described above, the reverse trigger 234 can cause both of the drive motors 30, 60 to reverse their direction. When the reverse trigger 234 is engaged while the two-stage trigger 232 is actuated during the first stage, the rotational drive motor 60 as well as the chuck 90 and the working tool, can spin in a reverse direction. When the second stage of the forward trigger 232 is actuated, and the reverse trigger 234 is still engaged, the rotational drive motor 60 as well as the chuck 90 and the working tool 110, can spin at maximal speed in a reverse direction and the axial drive motor 30 can begin to spin proportional to the degree of actuation of the second stage of the forward trigger 232. The action of the axial drive motor 30 can cause the guide harp 300 and the distal guide 170 to move in the distal direction (i.e. towards the work in direction of Arrow D, see FIG. 1B). The axial movement of the guide harp 300 can push the instrument 10 away from the work and draw the working tool out of the work. In another implementation, the motors 30, 60 can have independent reverse functions and can be controlled independently via independent actuators or triggers.

The instrument 10 can also include an oscillation select switch 240. The oscillating function can also be actuated by certain trigger combinations or an oscillation trigger. When the oscillation select switch 240 is in the "off" position, the instrument 10 can function as described above. When the oscillation select switch 240 is in the "on" position, the rotational drive motor 60 can move in the appropriate direction when the triggers 232, 234 are actuated and the axial drive motor 30 function is not affected. If the forward trigger 232 is actuated, the instrument 10 can move in the forward direction, i.e. the rotational drive motor 60 can move forward but the axial drive motor 30 can cause the guide harp 300 and the guide 170 to move in a proximal direction as before. If the reverse and forward triggers 232, 234 are actuated, the instrument 10 can move in the reverse direction, i.e. the rotational drive motor 60 moves in reverse but the axial drive motor 30 can cause the guide harp 300 and the guide 170 to move in the distal direction as before. The oscillation select switch 240 can affect the function of the rotational motor 60 not the axial drive motor 30. When selected it can cause the rotational motor 60 to move.

Although the above describes the use of "triggers" or "actuators" to cause a particular action of the instrument 10, it should be appreciated that triggers and actuators can include foot pedals to cause a particular action in the instrument. The instrument 10 may also be actuated or triggered by programming the instrument 10 to perform a particular action via a user interface on the instrument 10 or using an external computing device remote from the instrument 10 that is in wired or wireless communication with the instrument, which will be described in more detail below.

Irrigation System

The instruments described herein can include an irrigation system. The irrigation system allows for the surgical field to be kept cool while the instrument 10 is in use and reduce the risk of tissue damage such as bone burning and bone death. The irrigation system can also reduce the risk of hardware failure, the need for re-operation, infection, limb loss and death. The irrigation system can include one or more irrigation nozzles located at or near the engagement end of the body 20. In one implementation, the irrigation nozzles spray fluid from the distal tip of the body 20. In another implementation, the irrigation nozzles can be routed internally through the working tool. The irrigation fluid can be sprayed through a channel running through the working tool and exiting at a port near the distal end of the tool. In a further implementation, the guide harp 300 can have one or more irrigation nozzles. The irrigation nozzles can also be coupled to the distal guide 170. The irrigation nozzles can deliver irrigation fluid (i.e. a liquid or a gas) through irrigation tubing from a sterile fluid bag or other irrigation fluid source. In an implementation, carbon dioxide gas can be used to irrigate the work to remove heat. The irrigation tubing can be coupled to the instrument 10 via an irrigation port near a proximal end of the body 20. The irrigation tubing can be angled downward to avoid crimping and for more efficient manipulation of the instrument 10 by the user. An external fluid pump or gravity can be used to pressurize the irrigation system. The irrigation system can be kept outside the sterile surgical field except, for example, the irrigation tubing connected to the instrument 10. Such an arrangement can contribute to the engagement end and the working tool remaining relatively free from bulk or other awkward equipment enabling more accurate placement and easy use of the instrument 10 in the surgical field. The irrigation system of the instrument 10 can also include a suction mechanism at or near the surgical field. Suction can be applied through the irrigation nozzles or can be applied through additional channels. The irrigation system can be controlled manually by the user such as with an irrigation actuator positioned, for example, on a handle 25 of the instrument 10 or by a foot pedal or other mechanism. The irrigation actuator can be a depressible trigger or button that can turn on or off the flow of irrigation fluid from the irrigation tube. The same actuator or another actuator can turn on or off the suction applied to the surgical field. The irrigation system can also be controlled automatically for example by one or more sensors near the work site communicating with an electronics package of the instrument to be described in more detail below. Automated irrigation is generally a desired option for users as it can effectively reduce drill bit temperature, bone temperature and the risk of bone burning.

Power

The instrument 10 can be a corded or cordless powered instrument. In an implementation, the instrument 10 includes and is powered by a removable battery pack. The battery pack can be enclosed within a battery cover capped on the bottom by a battery case cover 245 that can be removed, for example, upon depression of a battery release button. The circuit board for the electronics can be sandwiched above the battery such that the electronics all drop out upon removal of the battery. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The instruments can also include rechargeable batteries using either a DC power-port, induction, solar cells or the like for recharging. Power systems known in the art for powering medical devices for use in the operating room are to be considered herein. It should be appreciated that other power systems known outside the art of medical devices are to be considered herein as well.

Motors and Sensors

Figure 2:
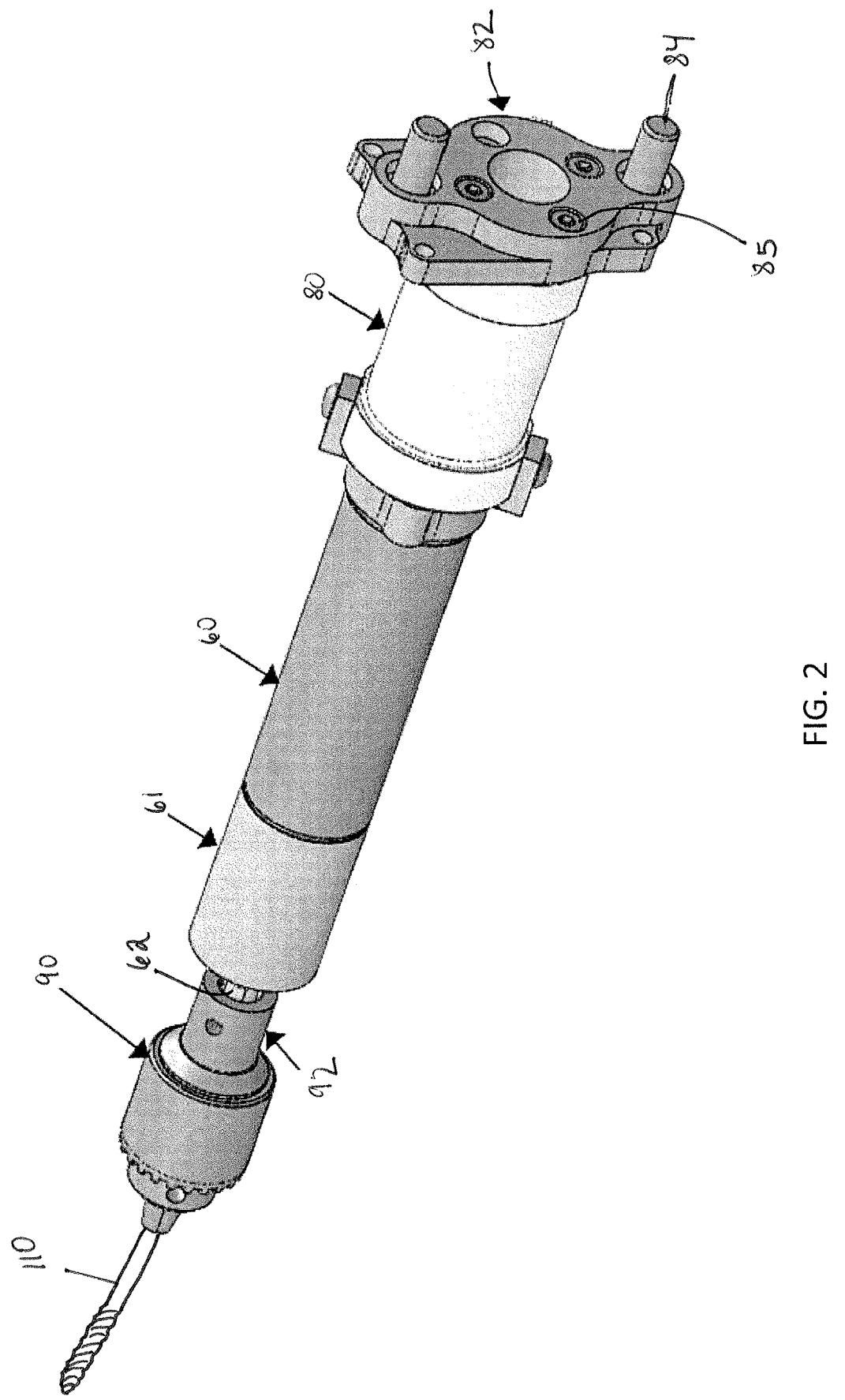
FIG. 2 illustrates a perspective view of a drilling sub-assembly for use with the instrument of FIG. 1A.
Figure 5A:
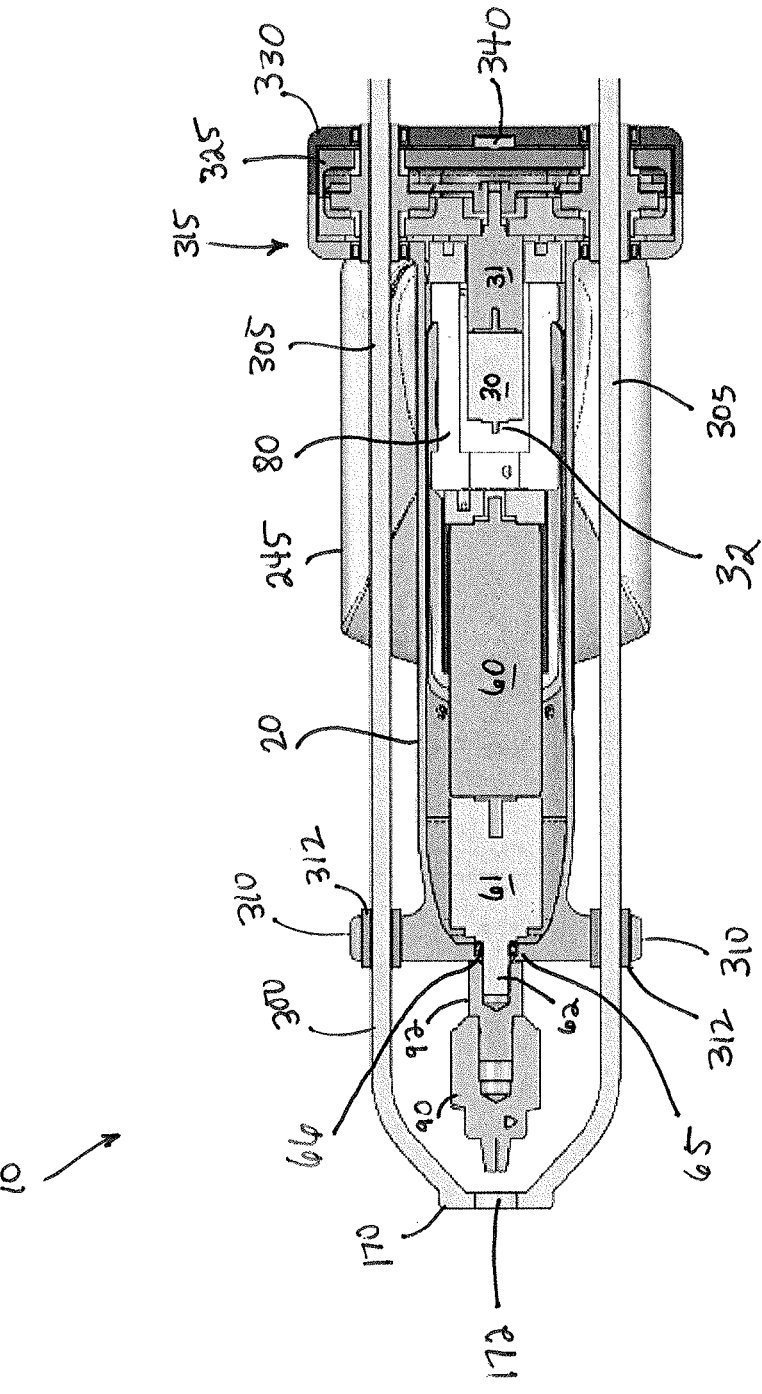
FIG. 5A is a top, cross-sectional view of the instrument of FIG. 1A.

FIG. 2 illustrates a perspective view and FIG. 5A illustrates a cross-sectional view of an implementation of a drill motor sub-assembly. The chuck 90 is shown at the forward end of the sub-assembly having a working tool 110 attached and coupled by a chuck adaptor 92 to the drive shaft 62 of the rotational drive motor 60. A gearbox 61 can be incorporated to convert the high-speed, low-torque operation of the motor 60 to a higher torque working tool 110 speed. When the motor 60 is activated it can rotate on an axis turning the gearbox 61, the chuck 90 and the working tool 110. The chuck 90 and the working tool 110 rotate around the longitudinal axis A (see, for example, FIG. 1A).

The instrument 10 can include one or more sensors (e.g. torque sensor, axial force sensor for the guide harp 300, axial force sensor for the working tool 110, load cell, etc.) such that a force applied to the distal guide 170, and/or the rear housing cover 330 can be tracked, measured, displayed and/or controlled in real-time during use of the instrument 10. In addition, a force applied to the working tool 110 and/or the motor 60 can be tracked, measured, displayed and/or controlled in real-time during use of the instrument 10. In addition, the rotational speed, time, velocity, acceleration, deceleration or torque of the working tool 110 can be measured. The sensor(s) can provide the user with information pertaining to the passage of the working tool 110 through different layers of tissue. The sensor(s) can also provide the user with information pertaining to the linear force being applied to the work by the working tool 110 and provide the user with information pertaining to the linear force being applied to the work by the distal guide 170 (or distal tool guide, when present). The sum of these forces is the total force being applied by the instrument 10. Knowing the total force and the two components of the total force can allow for "dual-force robotic control" or the maintenance of constant working tool force by controlling the axial drive speed.

In one implementation and as best shown in FIG. 5A, the instrument 10 can directly measure torque. The motor 60 can be mounted to the body 20 by a multi-dimensional torque sensor 80 having a motor mount 82 configured to attach the motor 60 to the drill body 20. The motor mount 82 can be configured to couple to a rear portion of the body 20 such as by one or more fasteners 85 (see FIG. 2). The motor mount 82 can further include one or more guide pins 84 configured to interface with the harp feed drive sub-assembly 325 as will be described in more detail below. The torque sensor 80 can be similar in design to a Futek reaction torque sensor FSH00608. When the working tool 110 engages the work in the z-axis, or axial direction, the torque sensor 80 can measure the torque and differentiate the elements of torque in the x-y plane. The torque associated with the work being done provides information pertaining to the passage of the tool 110 through varied layers of tissue. For example, it detects the movement of the working tool 110 through: cortical bone into medullary canal or cancellous bone; medullary canal or cancellous bone into cortical bone; cortical bone into soft tissue; and, it also detects if the travel in the z-axis is associated with any differential torque in the x-y plane, indicative of skiving.

Figure 4A:
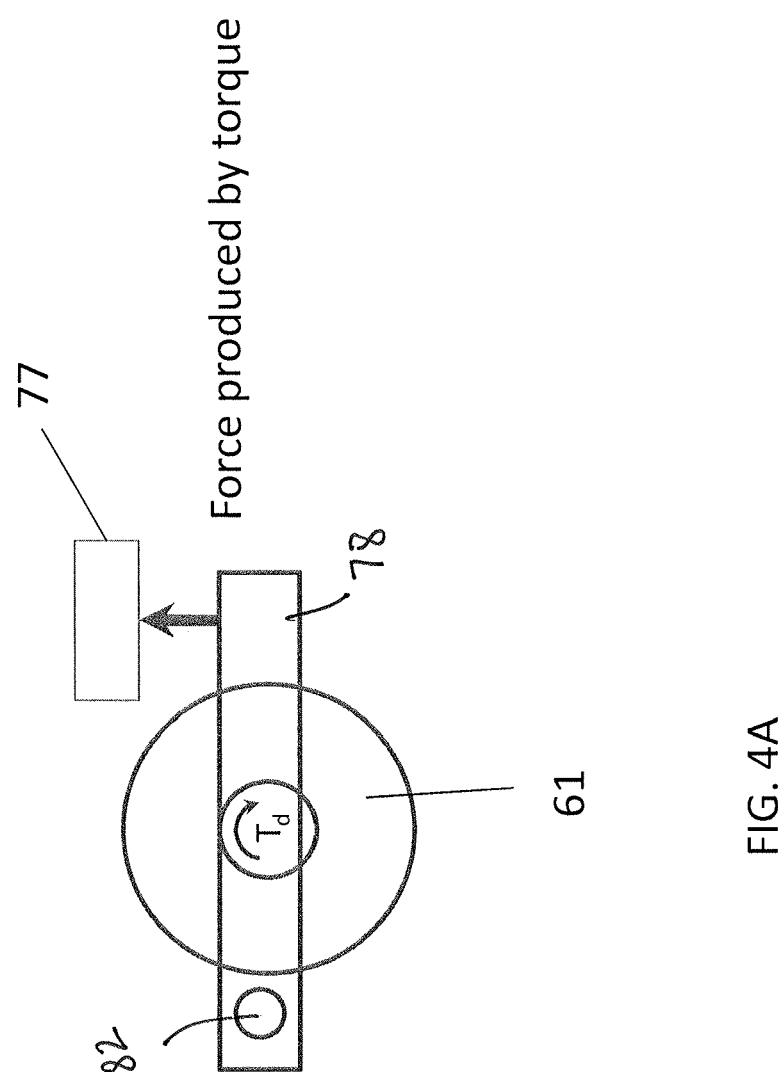
FIG. 4A is a schematic of a direct torque sensor measuring forces produced by drilling torque.

In another implementation of direct torque measurements, the gearbox 61 can be held as a reference point for the torque measurement and only the drilling torque Td is measured (see FIG. 4A). Measurements of the drilling torque Td can be taken at the output of the gearbox 61 such that internal gearbox losses are not included in the torque measurement although the motor 60 may still drive against the internal drag. A discrete sensor 77 can be incorporated in the instrument 10 to convert the drilling torque Td into a measurement signal. For example, a mechanical beam or level arm 78 can be connected to the motor mount 82 used to support the motor 60 and gearbox 61. The discrete sensor 77 can be positioned under the arm 78 such that the rotational motor 60 gearbox 61 presses against the sensor 77 to provide direct measurements of torque by converting the torque Td into a linear force. The linear force can be converted into an electrical signal using a strain gauge load cell or scale or other torque sensor to measure the resulting linear force. The direct torque measurement does not measure the energy lost internally to the gearbox 61 or the other motor components. The motor 60 can exert torque between its shaft and housing, which can be rigid mounted to the gearbox 61. In this implementation, the torque required to overcome the internal losses of the gearbox 61 can be transferred through the housing of the motor 60 and gearbox 61 and the mechanical path does not include a torque sensor 77. The torque sensor 77 can, instead be positioned between the gearbox housing 61 and the working tool 110 by attaching the torque sensor 77 to the drill body 20. The user can hold the body 20 of the instrument 10, which is rigidly attached to the gearbox housing 61. The torque sensor 77 can be located on a bushing allowing for the exit of the working tool or tool chuck from the body 20.

Figure 4B:
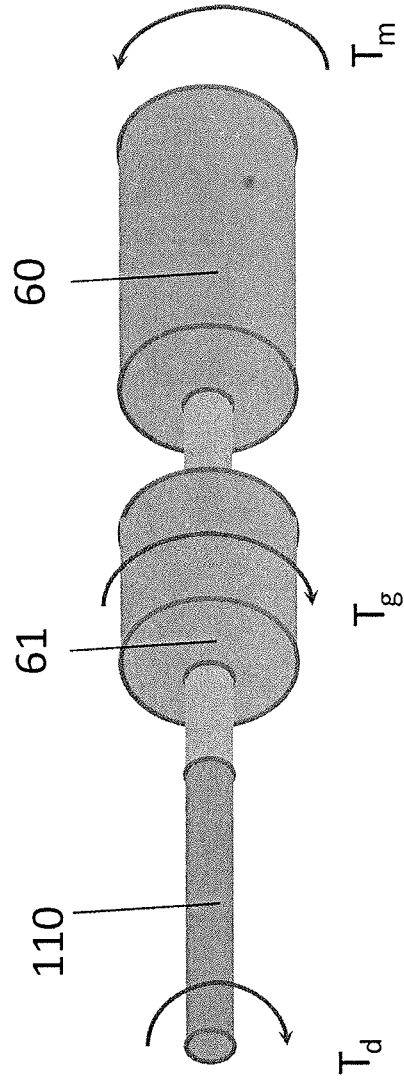
FIG. 4B is a schematic view of a drive mechanism showing torque forces generated by a working tool, gearbox and motor.

In other implementations, indirect measurements of torque can also be performed. For example, the motor 60 can be held as a reference point and the motor torque measured electronically. The instrument can measure current required to operate the motor 60 and can include drilling torque and gearbox losses. For example, as shown in FIG. 4B, the motor 60 can rotate and produce a motor torque Tm that is in the direction of rotation of the working tool 110 coupled to the motor 60. Drilling torque Td is opposite the direction of rotation of the working tool 110. The gearbox 61 can exhibit an additional torque component Tg due to internal energy losses, such as mechanical losses in the form of drag that counteracts torque and can result in a loss of energy between the motor 60 and the working tool 110. Gearbox torque Tg is also opposite the direction of rotation of the working tool 110. The motor 60 can be held as the reference point and the motor torque Tm measured electronically. In this implementation, the instrument measures the current required to operate the motor 60, for example a brushless DC motor with a Hall Sensor that operates a drive train, and the motor 60 acts as both the actuator and the sensor. Motor torque measurements in this implementation include both drilling torque Td and gearbox Tg losses. The gearbox inefficiencies can affect the accuracy of the torque measurements. The error in estimating the drilling torque component can be more pronounced for larger gear ratios in that more gears have more surface contact and thus, more drag.

Although motor self-torque measurement can be more convenient since no additional sensor is needed, the accuracy can be lower than for a direct torque measurement in which a torque sensor is used such as a mechanical beam or level to convert the torque into a force and use a load-cell (scale) to measure the resulting linear force. Direct torque measurements from a manufacturing standpoint can also allow one to design the gearbox independently from the torque measurement sensitivity. Direct measurements of torque can be obtained even with maintaining a non-constant RPM.

In other implementations, a torque sensor 80 positioned between the motor 60 and the motor mount 82 can be incorporated. The whole assembly (torque sensor 80, motor 60, and motor mount 82) can be suspended from front to back. In this implementation, the torque sensor 80 is not positioned between the second motor and the working tool and it is not positioned on the housing. In this implementation, the only parts that are in contact with the housing are the motor sub-assembly mount 82 and the drive shaft from the motor, which can contact a flanged & sealed bearing within a forward end of the body 20. Thus, the motor sub-assembly is "floating" in that it contacts only the housing at the back end and the bushings mounting the motor sub-assembly at the front end.

The axial drive motor 30 in combination with the harp feed drive sub-assembly 325 can power the guide harp 300 to move in an axial direction either forward, for example, for zeroing, or backwards such that the distal tip of the working tool 110 extends beyond the distal engagement region in order to engage the work. Again with respect to FIG. 5A-5B, the drive motor 30 coupled to gearhead 31 can be positioned within an interior of the torque sensor 80. The torque sensor 80 can be mounted via the motor mount 82 to a rear portion of the body 20. With respect to FIG. 5D, the harp feed drive sub-assembly 325 can couple to the a rear portion of the body 20 by guide bushings 326 configured to receive and couple with the guide pins 84 of the motor mount sub-assembly 82. Further, with respect to FIGS. 3, 5B, 5C, 5E, and 5F, the harp feed drive sub-assembly 325 can couple such that the nut threads 327 positioned within bushings 331 of the harp-feed drive sub-assembly 325 align with and extend through the corresponding openings 333, 335 of the rear guide 315 and rear housing cover 330, respectively. With respect to FIGS. 3, 5H, and 5I, the harp feed drive sub-assembly 325 coupled to the rear portion of the body 20 can be enclosed by the rear housing cover 330 coupled to the body 20 with one or more fasteners 86. The guide harp 300 is configured to be received through the nut threads 327 and the openings 333, 335.

Figure 3:
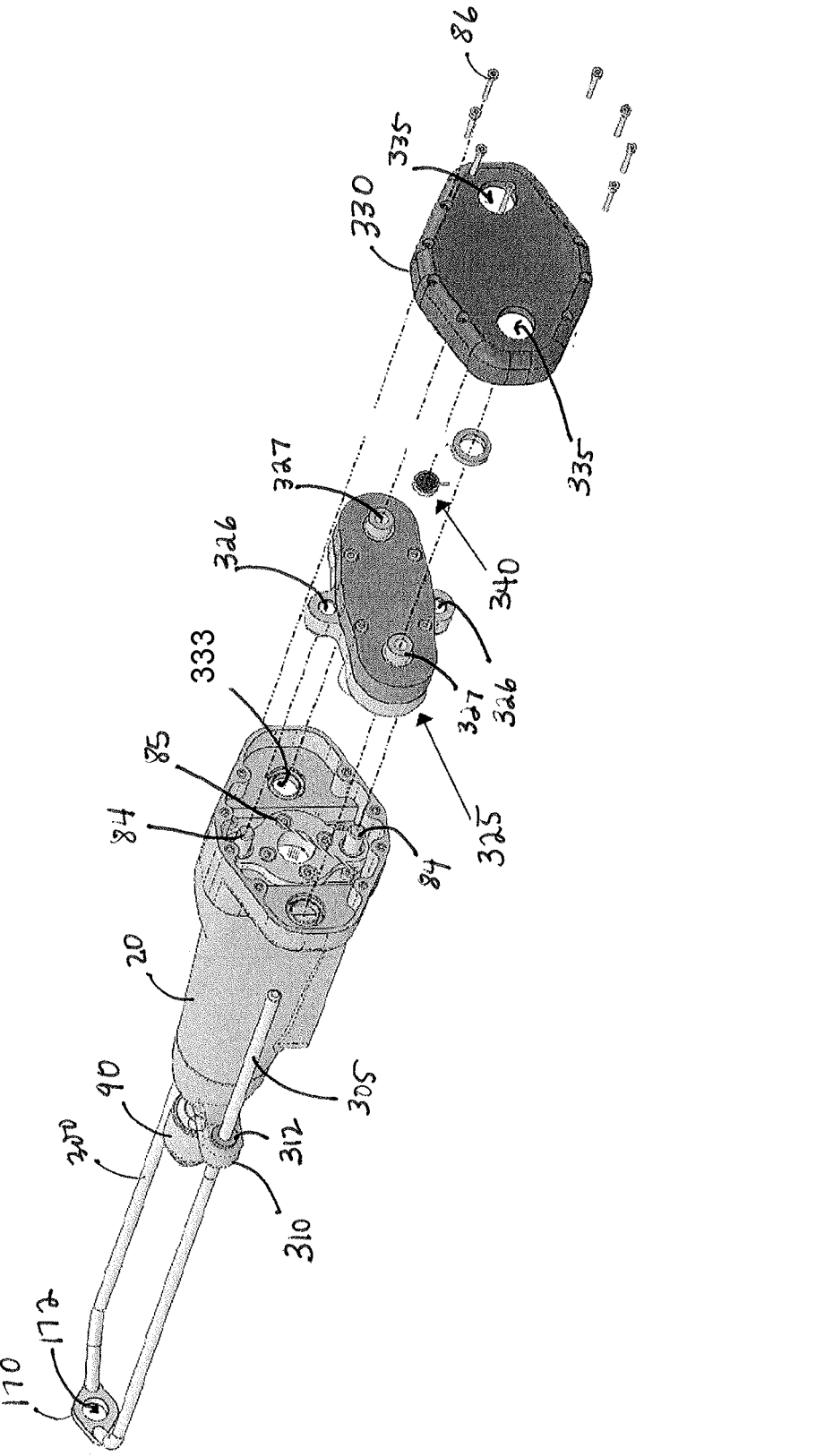
FIG. 3 is a partially exploded, partial view of the instrument of FIG. 1A.
Figure 5B:
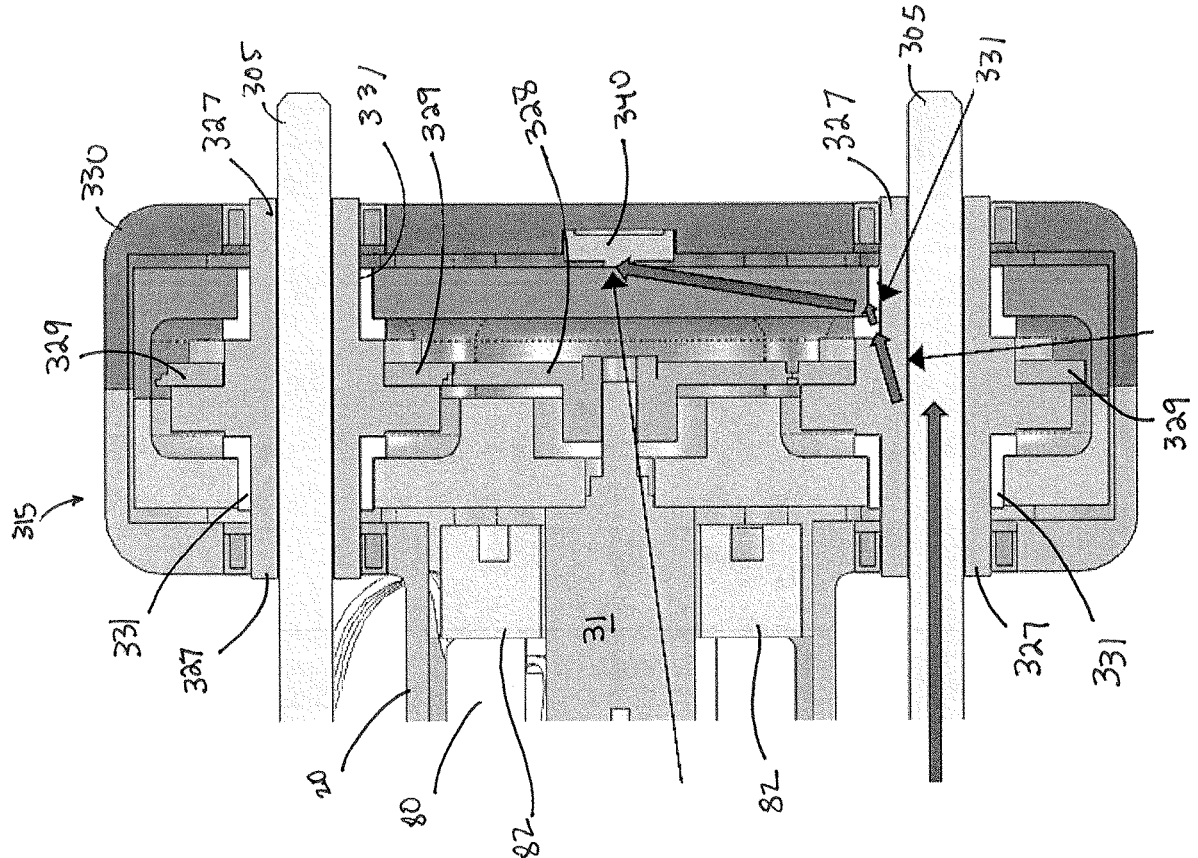
FIG. 5B is a detailed view of the instrument as shown in FIG. 5A.
Figures 5C, 5D:
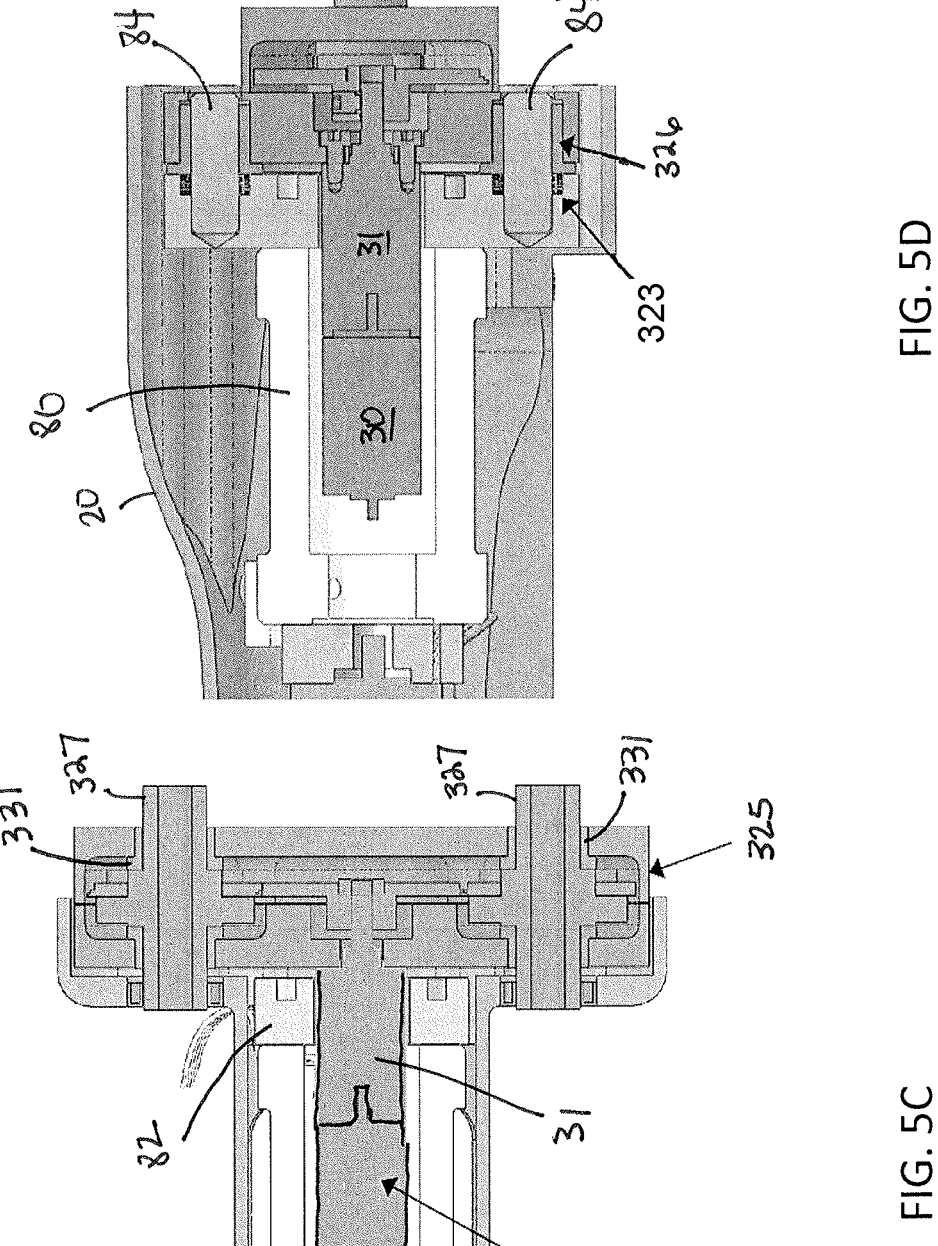
FIG. 5C is a top partial view of an instrument.
FIG. 5D is a side partial view of an instrument.
Figures 5E, 5F:
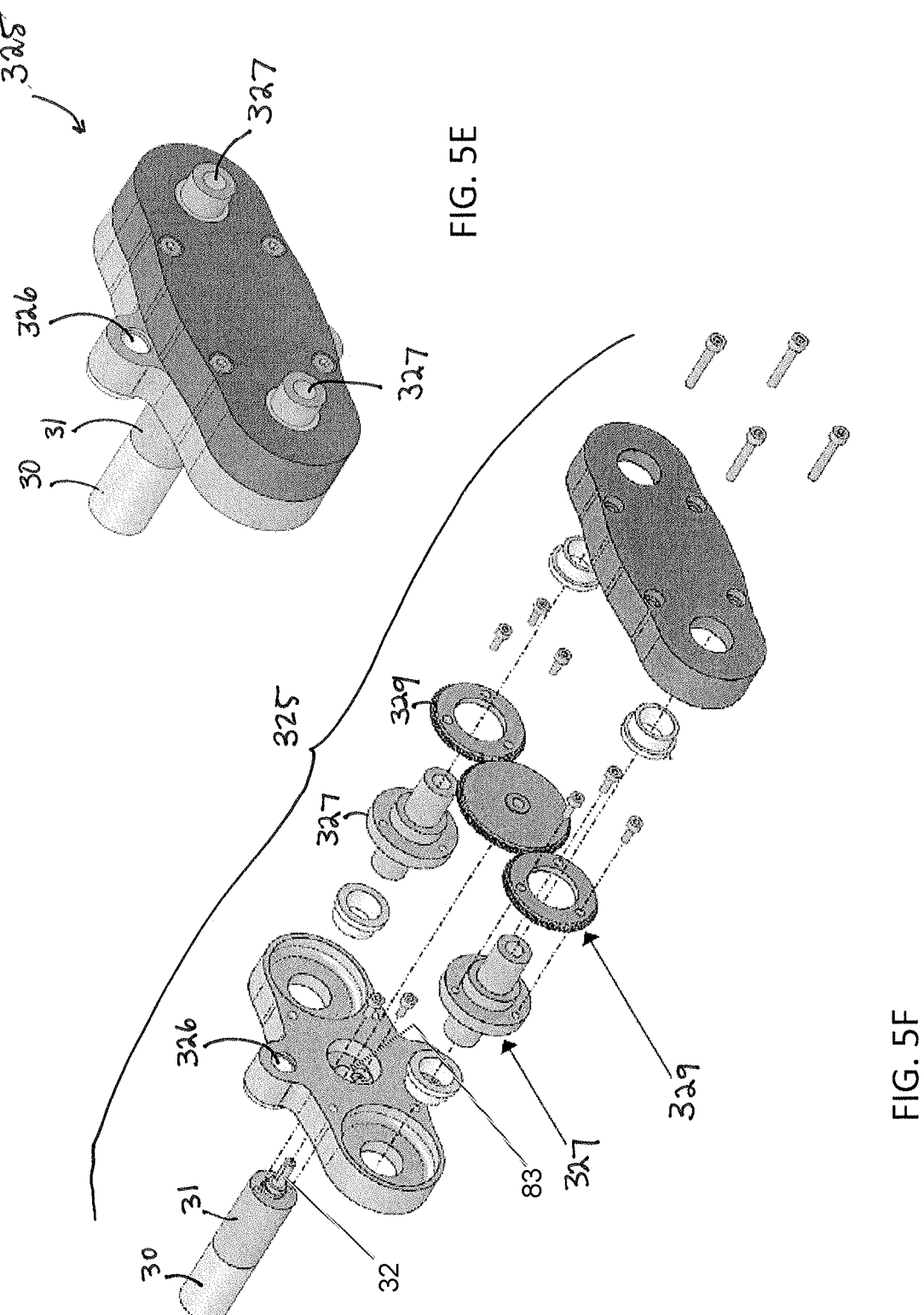
FIG. 5E is a perspective view of a harp feed drive sub-assembly.
FIG. 5F is an exploded view of a harp feed drive sub-assembly.
Figure 5G:
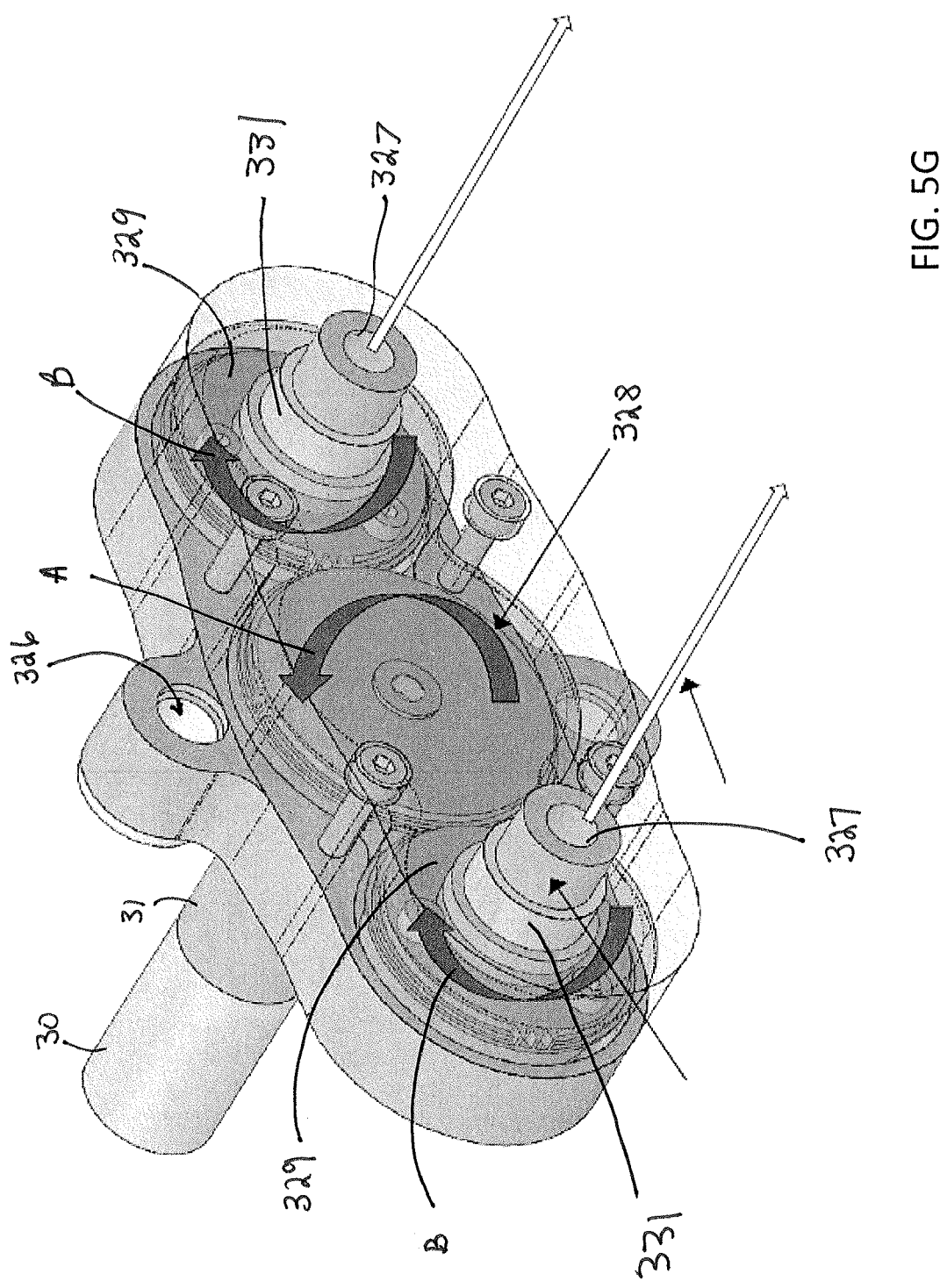
FIG. 5G is a perspective view of the harp feed drive sub-assembly of FIG. 5E showing rotation of the gears.
Figures 5H, 5I:
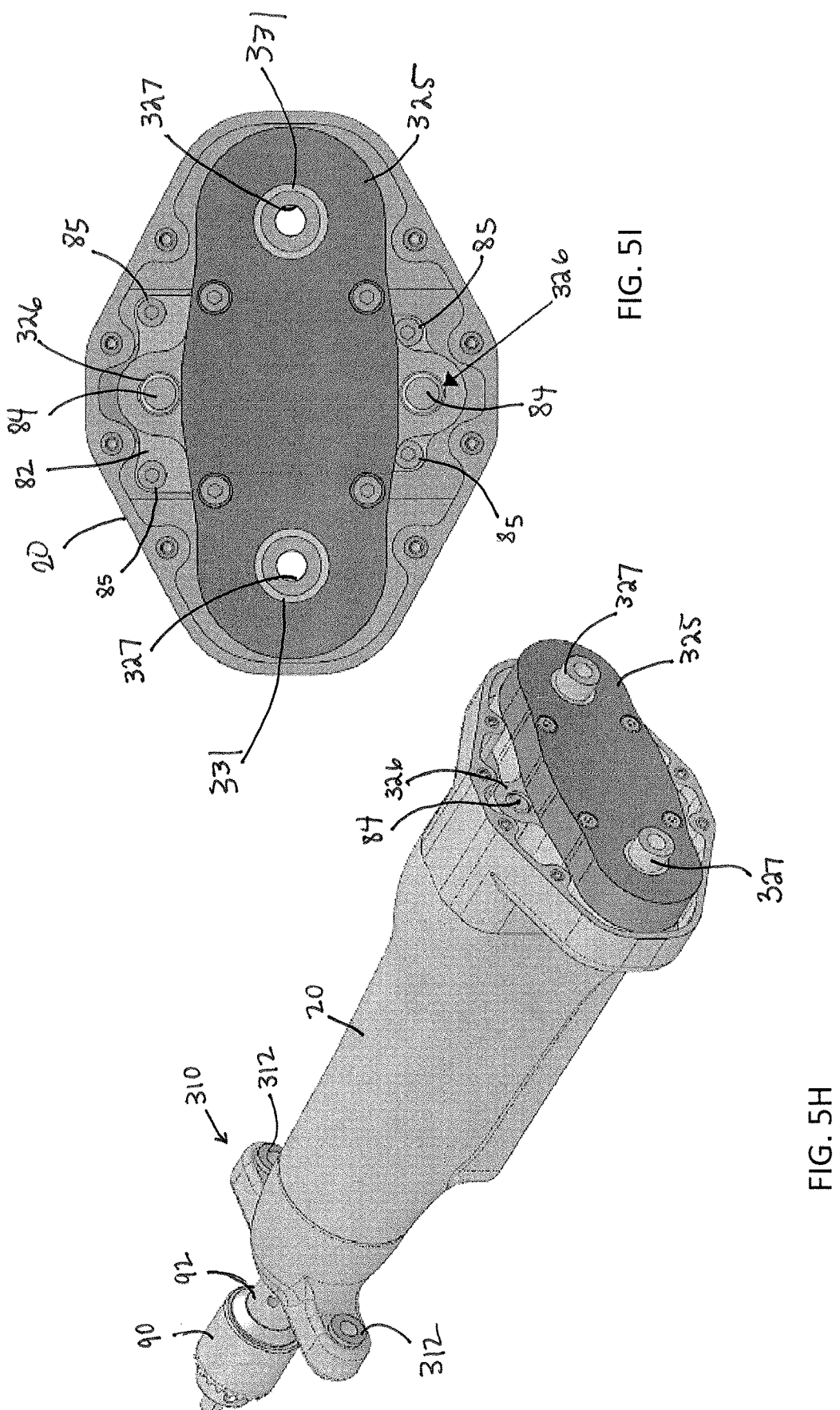
FIG. 5H is a perspective view of the harp feed drive sub-assembly of FIG. 5E coupled to a rear portion of the body.
FIG. 5I is a rear view of the harp feed drive sub-assembly of FIG. 5E coupled to a rear portion of the body.

With respect to FIGS. 3, 5F, and 5G, the harp feed drive sub-assembly 325 can include a central drive gear 328 operatively coupled with two feed gears 329. The drive gear 328 can turn in a first direction (arrow A) with the motor 30 and gear head 31 such that the two feed gears 329 turn in a second, opposite direction (arrow B). Drive shaft 32 of the gearhead 31 of the axial drive motor 30 can extend through a bore 83 in the motor mount sub-assembly 82 such that the gearhead 31 can operatively couple with the central drive gear 328 of the harp feed drive sub-assembly 325. The central drive gear 328 contacts and drives the two feed gears 329 configured to cause travel of the guide harp 300 through the nut threads 327 positioned within the bushings 331 of openings 333, 335 through the rear guide 315 and rear housing cover 330. The travel of the guide harp 300 can be due to engagement between external features such as threads on the rods 305 and the nut threads 327 of the harp feed drive sub-assembly 325. FIG. 5B is an enlarged view of the coupling between the gearhead 31 and the central drive gear 328 of the harp feed drive sub-assembly 325 shown in FIG. 5A. FIG. 5C is a top view and FIG. 5D is a side view of part of the instrument 10. FIG. 5F is an exploded view of the harp feed drive sub-assembly 325 shown in FIG. 5E. FIG. 5G illustrates the gears of the harp feed drive sub-assembly 325 of FIG. 5E. FIG. 5H illustrates a perspective view of the harp feed drive sub-assembly 325 coupled to a rear portion of the body 20. FIG. 5I is a rear view of the harp feed drive sub-assembly 325 coupled to the rear portion of the body 20.

One or more axial force sensors can be incorporated within the instrument to measure forces applied to the guide harp 300 as well as to measure forces applied to the working tool 110. In one implementation and as best shown in FIG. 5A, the drive shaft 62 of the rotational drive motor 60 and gearbox 61 can extend through a bushing 65 within a forward end of the body 20. An axial force sensor 66 can be incorporated within the bushing 65 such that a force applied at the working tool 110 can be measured during use, for example along the z-axis (i.e. the longitudinal axis A of the working tool 110). Additionally or alternatively, an axial force sensor 340 can be incorporated within the instrument 10 that measures force applied to the guide harp 300, for example along the z-axis. As best shown in FIGS. 5A and 5B, the axial force sensor 340 can be positioned between the harp feed drive sub-assembly 325 and the rear housing cover 330 such that application of pressure against the guide harp 300 can be translated through the nut threads 327 and bushings 331 such that the feed drive sub-assembly 325 pushes on the sensor 340, for example along the z-axis. One or more springs 323 can be incorporated such that the assembly is urged towards the force sensor 340 when no pressure is applied on the guide harp 300 to apply a small force that is zero force and zeroed out.

The instrument 10 can also instantaneously measure the depth the working tool 110 travels into the work by a transducer or encoder, such as an incremental rotary encoder, an absolute rotary encoder, mechanical, magnetic, electrical, or optical rotary encoder, or the like (see for example BEI Optical encoder; www.motion-control-info.com/encoder_design_guide.html). The depth the working tool 110 travels into the work can also be measured by a synchro, a resolver, a rotary variable differential transformer (RVDT) or a rotary potentiometer, or the like. In an implementation, the rotary encoder is an incremental rotary encoder with dual channels in quadrature with an additional data track to provide an internal position reference for setting a "zero point". The rotary encoder can be an absolute rotary encoder. The encoder can measure rotation and convert that information into axial motion. The encoder can interface with the drive motor 30 and the drive shaft 32 and can provide instantaneous information on the position of the drive shaft 32 regarding the depth of axial movement of the drive motor 30 and thus penetration of the working tool 110 into a bore. This information can be fed to electronics within the instrument, as will be described in more detail below, such that count multiplication to determine the tool position can be performed. For example, the rotation of the drive shaft 32 can be measured and a calculation performed to determine the distance traveled. This distance traveled can be compared to a set point or zero point such that the position of the working tool 110 from the distal end of the instrument can be calculated. This calculation relates to depth of the distal end of the working tool past the distal end of the distal guide 170 (or distal tool guide, if present). If the operator keeps the distal end of the distal guide 170 in contact with the starting point or zero point of the respective target tissue (e.g. bone) then the calculation will give the depth of the working tool in the target tissue.

Electronics

Figure 6:
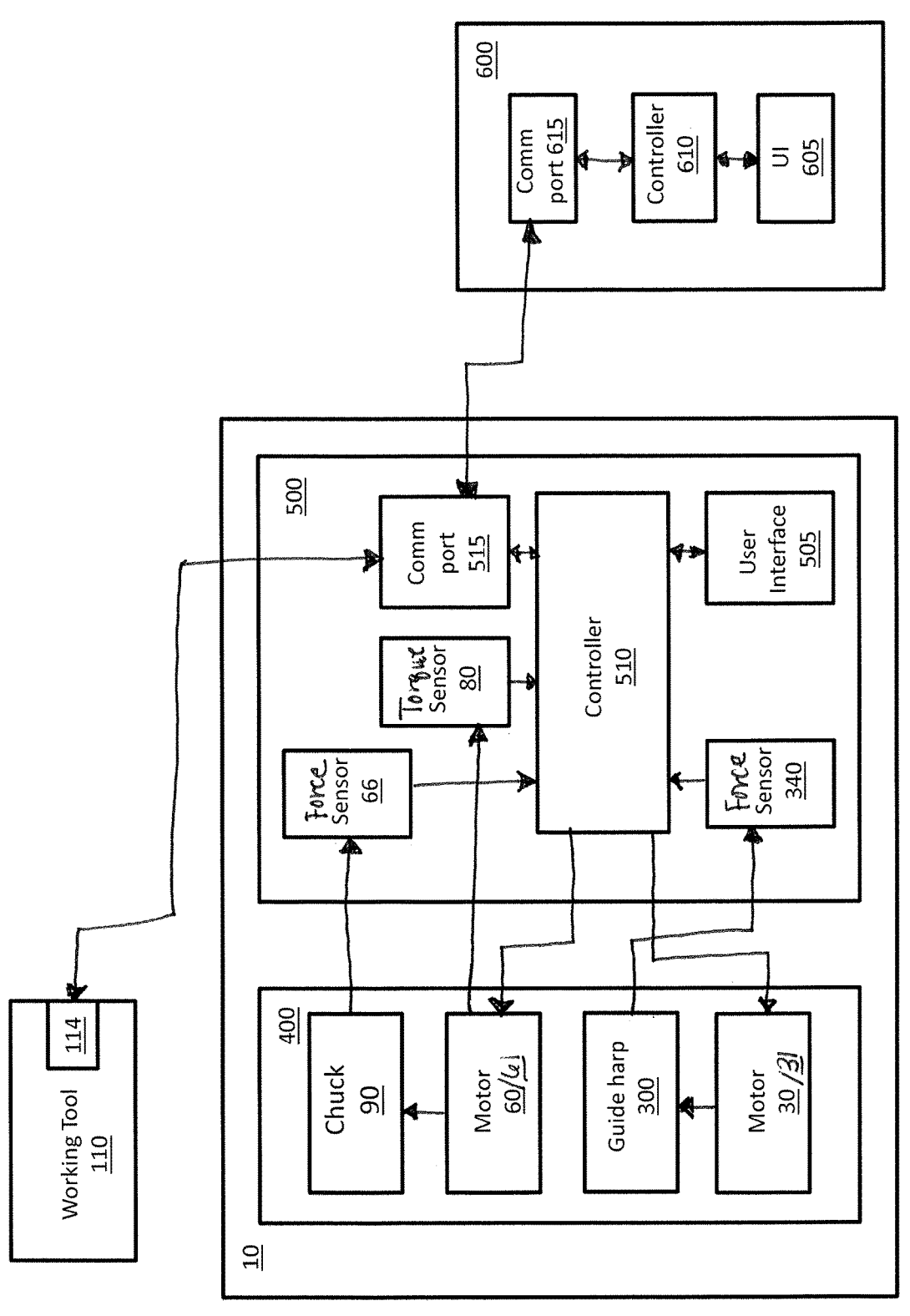
FIG. 6 is a box diagram schematic showing communication capabilities of the instrument.

FIG. 6 is a block diagram illustrating an implementation of the instrument 10 having a drive module 400 in communication with an electronics module 500. The drive module 400 can include the chuck 90 configured to couple with the working tool 110 and configured to be rotated by rotational motor 60 gearbox 61. The drive module 400 can also include the guide harp 300 configured to be reversibly driven in an axial manner by axial motor 30 and gearbox 31. The electronics module 500 of the instrument 10 can include a user interface 505, a controller 510, communication port 515, and the one or more sensors of the instrument including, but not limited to the force sensor 66, force sensor 340, and torque sensor 80. The controller 510 may be in operative communication with one or more components of the drive module 400 as well as in operative communication with one or more components of the electronic module 500 including the sensors, communication port 515 and user interface 505. The torque sensor 80 can measure and communicate information related to the torque of motor 60 to the controller 510 of the electronics module 500. The one or more signals from the torque sensor 80 can be processed into one or more processed signals representative of energy, power, accumulated energy, material strength, etc. as will be described in more detail below. The axial force sensor 66 can measure and communicate information related to the axial force applied on the working tool 110 to the controller 510 of the electronics module 500. Similarly, axial force sensor 340 can measure and communicate information related to the axial force applied on the guide harp 300 to the controller 510 of the electronics module 500. The various sensors can communicate this information in real-time to the controller 510 such that the processed signals can be displayed in real-time to the user via the user interface 505 on the instrument 10 or a display on an external computing device in communication with the instrument 10.

The user interface 505 can receive manual input from a user and may include one or more pushbuttons, keypads, a touchscreen or other inputs. The triggers 232, 234 described above can be one of the inputs. The user interface 505 may include a display or other visual indicators such as one or more lights to provide instructions and/or information to the user, such as when to stop drilling. The user interface 505 may include auditory or tactile indicators as well. For example, the user interface 505 can provide the user with alerts and information regarding the status of the instrument 10 and instrument components during use such that manual and/or automatic adjustments can be made. The user interface 505 can include an LED or other type of display using, for example, electrical filaments, plasma, gas or the like. The user interface 505 can include a touch-screen type of display.

The controller 510 can include at least one processor and a memory device. The memory may be configured for receiving and storing user input data as well as data acquired during use of the instrument 10 such as from the one or more sensors. The memory can be any type of memory capable of storing data and communicating that data to one or more other components of the device, such as the processor. The memory may be one or more of a Flash memory, SRAM, ROM, DRAM, RAM, EPROM, dynamic storage, and the like. The memory can be configured to store one or more user-defined profiles relating to the intended use of the instrument 10. The memory can be configured to store user information, history of use, measurements made, and the like.

The communication port 515 configured to communicate with another device. In some implementations, the communication port 515 can communicate with the working tool 110 as will be described in more detail below. In some implementations, the communication port 515 can communicate with an external computing device 600. The external computing device 600 can incorporate a communication port 615, a controller 610 and a user interface 605 (such as a graphical user interface or GUI). The communication port 515 of the instrument 10 and also the communication port 615 of the external computing device 600 can be a wired communication port such as a RS22 connection, USB connection, Firewire connections, proprietary connections, or any other suitable type of hard-wired connection configured to receive and/or send information to the external computing device 600. The communication port 515 and also the communication port 615 of the external computing device 600 can alternatively or additionally include a wireless communication port such that information can be fed between the instrument 10 and the external computing device 600 via a wireless link, for example to display information in real-time on the external computing device 600. The wireless connection can use any suitable wireless system, such as Bluetooth, Wi-Fi, radio frequency, ZigBee communication protocols, infrared or cellular phone systems, and can also employ coding or authentication to verify the origin of the information received. The wireless connection can also be any of a variety of proprietary wireless connection protocols. In some implementations, the instrument 10 has no user interface and communicates with the external computing device 600 configured to display information related to the instrument 10. The external computing device 600 can also control the instrument 10 such that the communication between the instrument 10 and the external computing device 600 is two-way communication.

It should be appreciated that the external computing device 600 with which the instrument 10 communicates can vary including, but not limited to, desktop computer, laptop computer, tablet computer, smartphone or other device capable of displaying information and receiving user input. The user interface 605 of the external computing device 600 can display information regarding the use of the instrument 10 relayed in real-time and provided to a user instantaneously during use of the instrument 10. The information can vary, including for example, bore depth, energy, power, torque, force, time or other information as will be described in more detail below. The user interface 605 of the external computing device 600 can also include one or more inputs such as a touchscreen or other inputs including buttons, keys, touchpads, or the like such that a user can interact with the processor to perform certain actions related to the programming of the instrument 10. The user interface 605 of the external computing device 600 can include a touch-screen. The controller 610 of the external computing device 600 can include at least one processor and a memory device as described in more detail above with respect to controller 510.

The external computing device 600 can be a heads-up display that communicates with the instrument 10 (i.e. either wired or wirelessly) and having a graphical user interface (GUI) that can display data and provide interactive functions such as a touch screen for input of data and information such as the drill bit size. The heads-up display can be mounted as is known in the art such as with a boom or other mechanism that provides user convenience. For example, the heads-up display can be mounted on a boom that can be easily positioned and moved around during a surgical procedure. The heads-up display can be autoclavable such that the display can be positioned within the surgical field where a user is using the instrument 10. Alternatively, the heads-up display can be inserted into a sterile cover such that the display can be positioned within the surgical field where a user is using the instrument 10.

As mentioned, the communication port 515 can communicate with the working tool 110. In some implementations, the communication port 515 can communicate with a transponder or other data element 114 on the working tool 110 configured to be in communication with the communication port 515. As an example, the element 114 can store data about the working tool 110 such as diameter, length, number of previous uses, date of manufacture, as well as any other information regarding the working tool 110. The data can be stored within the element 114 and communicated to and received by the controller 510 of the instrument 10 upon "reading" the element 114 on the working tool 110. The identification of the working tool 110 can be used by the controller 510 to set or to adjust certain parameters. The data can be received as part of a set-up procedure and preparation of the instrument for actual use. This can be initiated automatically by software run by the controller 510 of the instrument 10 without any user input. For example, diameter of the working tool 110 can be important in providing information regarding bone density and length of the working tool can be important for zeroing the instrument prior to drilling. The communication can be one-way or two-way wireless communication. The communication can be a wireless communication such as a transmitter and/or receiver, radiofrequency (RF) transceiver, WIFI connection, infrared or Bluetooth communication device. The data element 114 of the working tool 110 can include an encoder or bar code type strip configured to be scanned and read by a corresponding reader device of the instrument 10 that is in operative communication with the controller 510. The data element 114 may alternatively be an RFID chip or the like that transmits data to a reader such as a data receiving processor or the like. Such encoder devices include the ability to securely transmit and store data, such as, via, encryption, to prevent unauthorized access or tampering with such data.

The memory of the controller 510 can be configured to maintain a record for a particular working tool 110. For example, the record can indicate when the tool 110 is sufficiently dull that it should not be used for a particular operation. Once a tool 110 has reached a particular threshold for dullness, such as data regarding total energy of the tool, the software can be configured to write onto the memory of the data element 114 of the working tool 110 such that upon subsequent use, the instrument 10 is alerted to the information that the working tool 110 should not be used. Thus, information can be sent between the instrument 10 and the working tool 110 in a two-way manner.

The systems described herein, including the instrument 10 or the external computing device 600, can include a controller 510, 610 having a processor, memory, and storage device, as well as input/output 505, 605. The processor, the memory, and the storage device and the input/output devices can be interconnected via a system bus. The processor can be capable of processing instructions for execution within the systems. Such executed instruments can implement one or more of the processes described herein related to use of the instrument. For example, one or more signals from a first sensor can be communicated to and transformed into one or more processed signals representative of or providing information relating to what was sensed including, but not limited to one or more of torque, energy, power, accumulated power, time, material strength, material density measurements, spindle speed, depth, feed control, force, 3D orientation of penetration, drilling energy, pull-out force, screw insertion energy, and the like.

The processor of the controller 510, 610 can be a single-threaded processor or a multi-threaded processor. The processor of the controller 510, 610 can be capable of processing instructions stored in the memory and/or on a storage device to display information to the user such as on a graphical display or other user interface provided via an input/output device. It should be appreciated that the graphical display need not be on the instrument, but can be on an external computing device in communication with the instrument. Alternatively, it should be appreciated that the output need not be graphical and can be any of a variety of indicators (lights, sounds, tactile feed-back).

It should be appreciated that one or more of the components of the instruments described herein can be configured to be reversibly removed from the instrument. For example, the body 20 can include one or more removable covers that can be used to access one or more of the various internal components. Further, one or more of the internal components can be modular and can be completely separated from the body 20 of the instrument 10. This allows for interchanging parts as well as cleaning and sterilizing the components of the instrument 10. For example, the electronics module 500 and/or the batter pack can be removable from the instrument 10, for example, during autoclaving. Similarly, one or more components of the drive module 400, the trigger assembly 212 and/or the battery pack can be reversibly removable for easier cleaning and autoclaving.

Alerts, Graphics and Guidance

As described above, the instruments described herein can include one or more sensors that communicate information to the controller 510 and/or the user using a variety of alert mechanisms and/or graphical displays via the user interface 505 of the instrument 10 and/or the external computing device 600. The alerts, displays, and guidance provided to a user allows for greater control during the procedure and understanding of the tissue material being penetrated such that informed choices can be made on the fly. For example, a user can visually observe the surgical process by watching read-outs from the one or more sensors, such as a graph or read-out showing torque, power, energy, force, in order to make decisions whether to continue, readjust, stop, or to select a different tool.

As described herein, the instrument 10 can include one or more axial force sensors 340, 66 to sense the axial force applied at the guide harp 300 and/or the working tool 110, respectively, to ensure proper engagement with the work. The axial force sensors 340, 66 can communicate with the controller 510 that can in turn provide an output, such as an axial force alert, to the user to indicate when an amount of pressure is being applied by the user, for example, to ensure that the distal end of the guide 300 and/or tool the 110 stay engaged with the work and the user maintains an appropriate level of pressure. In use, the user can inadvertently lighten manually-applied forward (or axial) pressure on the instrument 10 that can result in a slowing of progress into the work and consequently the drill guide 300 from backing away from the work. A user can maintain forward pressure on the instrument 10 such that the working tool 110 drives into the bone distally as the guide harp 300 retracts in a proximal direction. If a user does not maintain forward pressure, the instrument 10 can be pushed in a proximal direction resulting in the working tool 110 not moving into the work. It can be desirable, however, to use as little forward pressure on the instrument as necessary to avoid injury to the bone. The instrument can be programmed to provide the output to the user when an appropriate amount of pressure is being applied or when the pressure being applied falls outside a programmed range. Applying too much pressure or force on the work, which can be a fractured bone, can increase the risk for damage to the work or surrounding tissues. Applying too little pressure or force can cause the tool 110 to back off the work and prevent tool advancement at the desired rate.

The axial force sensors 340, 66 can communicate with the controller 510 in real-time, which in turn can provide an axial force alert for the user regarding the status of the guide 300 and/or the tool 110 and whether the applied axial force is at the desirable pressure for an optimum result. The axial force alert can be visual, auditory, tactile or other output. The axial force alert can include an alarm or other auditory signal, a light or other visual signal, a vibration or other tactile signal, or a combination thereof. In an implementation, the visual output can be a number and/or an LED light or graphical interface that reflects the amount of force. The visual output can be positioned in the line of sight with the work, for example on a display positioned near or on the rear panel 330 of the instrument 10 and/or a user interface 605 of the external computing device 600 as will be described in more detail below. The output of the axial force alert can be related and/or proportional to the axial force being applied such that the user is informed that no force or too little force is bad, light force is good and heavy force is bad. For example, the axial force alert can include a light that can change color or a plurality of lights that sequentially illuminate depending on the axial force applied. Alternatively, the axial force alert can include an auditory alert that changes pitch or frequency depending on the axial force applied. In some implementations, the numerical value of the force being applied in real-time can be displayed. The numerical values can be highlighted with a color that correlates with the amount of force being applied. For example, flashing white or yellow light can mean too little axial pressure is being applied. If insufficient force is being applied, the device can be automatically controlled to stop rotating to prevent thermal injury and only begin rotating when sufficient force is applied. A green light can be indicative of sufficient force and that the axial pressure is within a proper or desired range. A flashing red light can indicate that too much force is being applied. If excessive force is applied, the device can be automatically controlled to stop and/or an audible alarm sound to alert the user that the force has reached a level that can cause injury.

Similarly, the torque sensors can communicate with the controller 510 in real-time, which in turn can provide a torque alert for the user regarding the status of the motor 60. The torque alert can be an alarm or other auditory signal, a light or other visual signal, a vibration or other tactile signal, or a combination thereof. For example, the sensed torque similar to the sensed axial force can be displayed visually such as on a graphical interface in the line of sight with the work. The torque alert can also be proportional relative to the torque being applied. Further, the output for the axial force alert can be distinguishable from the output for the torque alert. For example, a first auditory signal can be provided by the axial force alert proportional to the axial force and a second auditory signal can be provided by the torque alert proportional to the torque applied. The auditory signals from the two alerts can be distinguishable by the user as being separate. For example, the axial force alert can be a different pitched auditory signal compared to the torque alert. In another implementation, the axial force alert can signal the user only when conditions at the work change, whereas the torque alert can be a continuous signal, such as a sound with a variable pitch that is proportional to the torque or energy being sensed. It should be appreciated that any number of sensors and a variety of alerts or graphical information can be used singly or in combination.

Figure 7A:
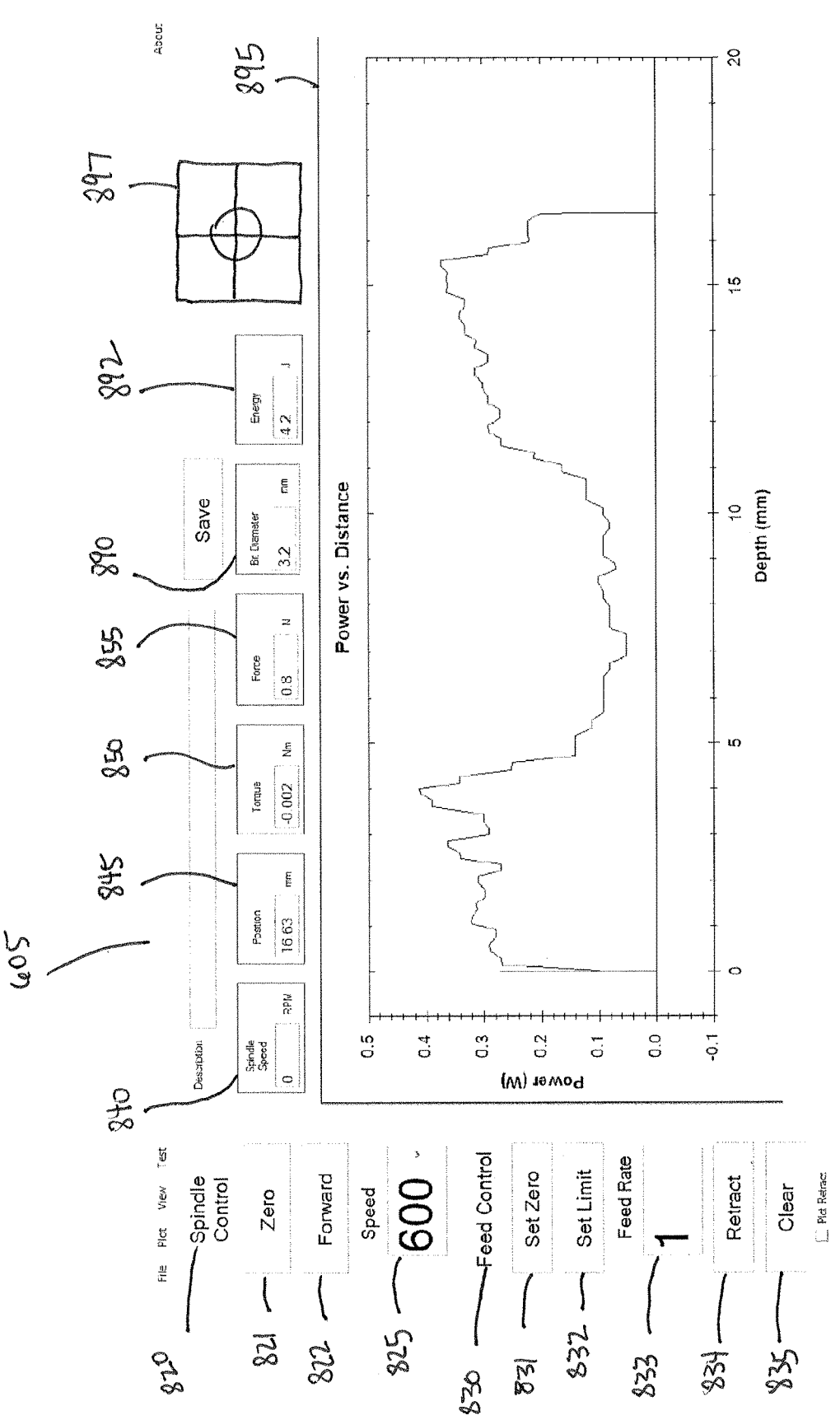
FIG. 7A is an implementation of a graphical user interface output for the instrument.
Figures 7B, 7C, 7D, 7E, 7F:
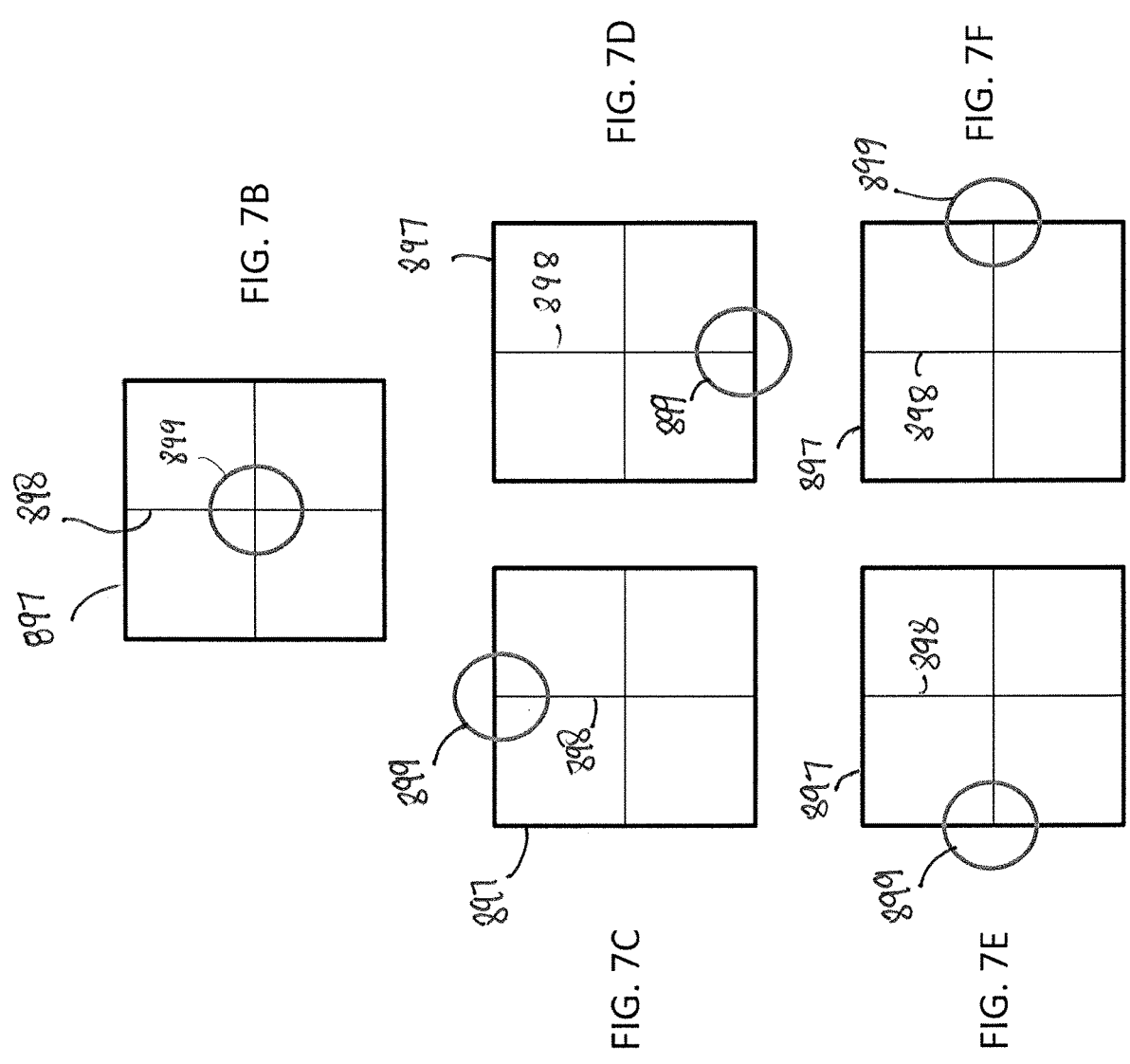
FIGS. 7B-7F illustrate various views of an implementation of a real-time guidance plot for use with the graphical user interface of FIG. 7A.

The axial force alerts and torque alerts can also be displayed on the external computing device 600, for example, via a wireless link. FIG. 7A illustrates an implementation of a page on the graphical user interface (GUI) 605 on the external computing device 600. In some implementations, the GUI 605 can be a simple touch-screen type of display. The user can view and/or manipulate directly one or more settings displayed on the GUI 605 to program the instrument 10. The GUI 605 can be organized according to a simple information architecture and hierarchy of pages or display representations. A user can navigate through one or more pages embedded within a program accessible by the controller 610 of the external computing device 600, including a home screen, plot screen, and test screen and others. The user may be presented with a number of variables and conditions that can be adjusted, confirmed, etc. including, but not limited to spindle controls 820 such as zeroing 821 and forward and reverse 822 controls, speed in rpm 825 of one or more motors on the instrument, feed controls 830 such as zeroing 831 and set limit 832, feed rate 833, retraction 834, and clearing 835 of all inputs and data to a default.

The GUI 605 can also display information relating to the status of certain components during use of the instrument. For example, spindle speed in RPM can be displayed in a window 840. Position of the working tool in mm relative to the zero point can be displayed in a window 845. Torque readings of the rotational motor from the torque sensor 80 in Newton meters can be displayed in a window 850. Axial force readings of the guide harp 300 in Newtons can be displayed in a window 855. Similarly, axial force readings of the working tool 110 can be displayed in another window. Axial force displayed in the window 855 can be highlighted, for example with a color according to whether the axial pressure being applied is too little, too much or within a desired range. Other windows 890 can be included that display information related to the working tool 110 such as length and/or bit diameter. Another window 892 can display accumulated energy in joules, which will be described in more detail below.

One or more plots 895 can be presented on one or more of the pages of the GUI 605. The plots can illustrate graphically any of a variety of data collected during use of the instrument 10. In some implementations, accumulated energy in Joules can be displayed as a function of position measured in mm (see FIG. 9) as a function of time. In some implementations, power measured in watts (W) can be displayed as a function of depth measured in mm, or as a function of time, to illustrate the movement of the working tool through the layers. It should be appreciated that position, depth, distance, and displacement are all used herein interchangeably to indicate travel of the tool through the work and are not intended to be limiting. As the tool penetrates the bone, the depth of the tool in mm can be shown graphically on the x-axis. The depth in mm can vary depending on the location of use as well as the patient. FIG. 7A shows the depth through an experimental "bone" having a near cortical layer, a cancellous layer and a far cortical layer. The depth of the near cortical layer was about 4 mm, depth through cancellous layer was about 7 mm, and depth through far cortical layer about 4.5 mm. Thus, total depth of penetration from start to finish was about 15.5 mm, these measurements correlated to measurements with calibers. Additionally, as the tool penetrates the near cortical bone the power in watts can rise almost instantaneously and thereafter plateau as the working tool drills through the near cortical bone. The increase in power shown in the experimental "bone" layers of FIG. 7A was between about 0.25 watts to about 0.4 watts. Once the tool leaves the near cortical bone and enters the cancellous bone, the power in watts can decrease as quickly and plateau again, for example, between about 0.05 watts to about 0.1 watts as the tool drills through the cancellous layer. As the tool enters the far cortical bone, the power in watts can once again rise and plateau. A user can visualize the penetration of the working too through the far cortical bone on the x-axis of the plot until the second drop in power starts to occur indicating the far cortical bone has been breached. The user can manually stop drilling upon seeing the second drop in power on the graphical display.

Typical human reaction time without such a graphical display of drilling power can result in 8-16 mm plunge beyond the far cortex, which can cause serious injury. Typical human reaction time using the graphical display of drilling power as a function of distance like that in FIG. 7A is only about 0.5 mm beyond the far cortex. Thus, even without software programming to stop axial advancement of the drill, human reaction time with the present graphical display of drilling power restricts plunge to a minimum depth thereby preventing serious injury. The drop in power sensed by the instrument is more sensitive and alerts a user sooner about break-through than would otherwise be possible when relying on a user's "feel" for the passage of the instrument through the bone. The user can see the break-through on the graphical display before they can feel the break-through, the depth control provided by the guide harp 300 limits penetration depth to a smaller and safer amount. It should be appreciated that the controller 510 of the instrument 10 can be programmed to stop drilling upon sensing this second drop in power indicative of exiting the far cortex. For example, the software of the controller 510 can prevent further retraction of the guide harp 300 and thus, further penetration of the tool into the work. The present device can be completely passive where the software can be programmed to perform the entire drilling process without relying on the surgeon to know when or whether to stop or the present device can be programmed to be manual without any control and rely on the surgeon to read the sensed outputs to know when or whether to stop, as will be described in more detail below.

The GUI 605 can include any number of features for assisting in preventing the user from entering, changing, or accepting any information that may be incorrect or inconsistent. For example, the user may be presented with confirmation pages and/or queries where the user is required to confirm one or more presented pieces of information to prevent the user from selecting one or more objects displayed on the screen. The GUI 605 can present important information to the user as to the status of the instrument (e.g. battery life, remaining life of the working tool, or dullness of the working tool, etc.). The alerts and presentation of the information can vary, for example, flashing lights and/or changing colors on the display screen. The information entered by a user or data collected during use of the instrument 10 and displayed on the GUI 605 can be saved as a file in the memory of the external computing device 600 and/or the memory of the instrument 10.

Again with respect to FIG. 7A, the GUI 605 can also include a real-time guidance plot 897 that allows a user to maintain a proper angle of penetration during use of the instrument 10. The torque sensor 80 can have various strain gauges that can provide information along the various axes that can, in turn, be communicated and displayed on the plot 897 in real-time. This type of guidance can be particularly useful in a joint or a curved region such as the pelvis, scapula or pedicle. It should be appreciated that the plot 897 can be displayed on the GUI 605 of the external computing device 600 and/or on a user interface 505 of the instrument 10, for example near a rear of the device in a user's line-of-sight. In some implementations, data from the axial force sensor 66 for the working tool 110 as well as data from the axial force sensor 340 for the guide harp 300 can be communicated and displayed on the plot 897 or on another plot. Data represented on plot 897 represent abnormal torque arising in the x-y plane as the working tool 110 moves along the z-axis. In some implementations, the plot 897 can include cross hairs 898 (see FIGS. 7B-7F) dividing the plot 897 into four or more quadrants such that forces in the x-y plane and aligned with the z-axis are shown having an indicator 899 such as a dot or other shaped element centered on the cross hairs 898. If the relative readings of the strain gauges indicates a greater force being applied along one axis over another away from the z-axis (i.e. the center of the x-y plane), the indicator 899 can travel within the plot 897 graphically illustrating the angle of force being applied. The user can view the plot 897 and the movement of the indicator 899 relative to the cross hairs 898 and make adjustments as needed to once again center the indicator 899 and thus the forces within the cross hair 898 (see FIGS. 7B-7F). This allows for adjustments to be made in real-time to keep the angle of penetration on target and prevent damaging neighboring tissues. This can be particularly important in preventing damage when drilling through a structure having a rounded shape such as the scapula, pelvis, pedicle etc. or where neighboring structures are of particular importance such as the bladder, nerves, or spinal cord. This plot 897 as well as the plots showing power, distance, time, force, and/or energy all aid the user in maintaining a safe and accurate drilling, reaming, sawing or other type of cutting or driving.

As mentioned above, the instrument 10 can incorporate a plurality of axial force sensors, for example to measure forces on the guide harp 300 as well as separately measure forces on the working tool 110. Thus, forces on the harp 300 can be sensed independently from forces applied on the tool 110 allowing for better control of drilling and the prevention of thermal injury. Thermal injury can result from tentative drilling. For example, when a surgeon is drilling through a bone there is a tendency to back off the pressure because of fear of breaking through and plunging. However, this can lead to ineffective drilling and instead expose the surrounding bone and tissue to excess heat due to rotation of the tool. For example, if the force on the harp and pressure against the surface of the bone is not maintained at a minimum threshold, the working tool will simply turn and not penetrate the target, which can contribute to thermal injury. Thus, forces applied on the guide harp 300 along the z axis and forces applied on the working tool 110 along the z axis are both important to track and control. However, tracking and controlling these dual forces need not relate only to drilling. It can be useful to track and control axial forces when using other driving tools. For example, dual force control can be useful to incorporate with catheter insertion tools such as IV catheters for anesthesia in which an outer guide is applied to the skin with a first force and an inner inserting is applied to the vessel at a second controlled force, this implementation can be completely without motors.

In another implementation of the dual force control technology, the distal guide 170 (or distal tool guide, if present) can press on and hold the work (e.g. artery or duct such as a bile duct), and a cutting tool (e.g. a blade or scissors) can extend through the central channel 172 and the controller 510 can delicately control the force of the cutting tool against the work, which is held stable by the distal guide 170. In another implementation, the instrument 10 is connected to a robotic arm. This allows the controller 510 to control both the force on the guide harp 300 (previously controlled by the operator) and the force applied to the working tool 110. This negates the need for two separate devices, one to function as a control arm, analogous to the distal guide 170, and another device to control the working tool 110 and prevents issues due to compliance in the system amplified by the distance between the working tool 110 and the control arm. For example with total hip arthroplasty, the tissue compliance of the muscles, ligaments and fatty tissues of the hip and pelvis can lead to errors in the placement of the acetabular cup. For intraabdominal surgery this leads to difficulty with precisely cutting open small sections of arteries and bile ducts for example.

Programming

As mentioned above, the instruments 10 described herein can be used such that speed, depth, axial force and/or angle of penetration can be manually controlled such as according to information provided by the instrument to the user. The instruments 10 can also be programmed to control penetration of the working tool 110. The controller 510 of the electronics module 500 can include motor control electronics and software programs that can be programmed to automatically adjust the instrument 10 in real-time to maintain use of the instrument 10 within set thresholds. For example, the instrument can include software capable of being programmed to continuously measure and/or control a variety of functions including, but not limited to, bone depth, material strength, bone density, skive, drill bit development, speed of rotation, acceleration, deceleration, irrigation, voltage, torque, thrust, feed rate, current, voltage, axial movement, axial force, angle of penetration and other functions of the instrument or a combination thereof. As such, the instruments described herein can detect and control penetration of the working tool through various tissue layers. The instruments can control, for example, axial feed rate of the guide harp 300, RPM of the motors 30, 60, and engagement of the work to allow a user to avoid certain unsafe instrument situations. For example, the instruments described herein can detect joint penetration in real-time allowing a user to avoid "pop through" or plunging situations, for example, in which the instrument suddenly penetrates the cortical bone and inadvertently damages soft tissue or joint structures. Joint penetration can occur perpendicularly as well as tangentially (also known as skiving). The instruments described herein can provide an overall system stability that allows for the accurate tracking and detection and control of instrument status during use.

In an implementation, the maximum depth of the bore that is to be created by the instrument 10 can be programmed with electronics in advance of drilling. The measurement can be zeroed by the user prior to use, for example, by depressing an axial measurement selector/reset button. This allows the user to zero the measurement according to the length of the selected tool 110. In one implementation, the distal end of the working tool 110 can be aligned with the distal guide 170 and the instrument zeroed. This can be performed manually by the user or electronically with set points and a feedback system (i.e. interface with the coupler). The alignment of the distal end of the tool 110 and the guide 170 can be such that the two are flush with one another or the distal end of the tool 110 can be some distance beyond the guide 170, for example between about 3 mm and 7 mm. The tool 110 can be positioned flush against the bone prior to drilling. As the tool 110 advances into the bone, the instrument 10 can be held flush against the bone. Once the cut is started and the tool 110 can be flush with the bone, the user can use the axial drive to further advance the tool 110 through the bone. The controller 510 can be zeroed as described above to include the additional axial length of the guide 170.

In another implementation, the user can feed in a proximal direction the guide 300 such that a portion of the working tool 110, for example 30 mm if working on a tibia or femur or 12 mm if working on a radius, extends beyond the guide 170. The user can then manually drill through the bone as with an axially static drill. Upon reaching that pre-programmed depth, if the distal cortex had not yet been breached, the axial drive can be used to penetrate the bone further. In another implementation, the electronics can contain a preset maximum distance that can limit the distal travel of the guide 300. For example, a stop and go signal (i.e. single click of the trigger) or a double stop and go (i.e. double click of the trigger) can release the depth stop and allow further travel. Any of a variety of schedules can be programmed into the electronics to control advancement of the tool through the work. For example, each time the guide 300 is withdrawn beyond the initial stop, the electronics can be programmed to allow only a further travel of for example 3 mm or 6 mm or other incremental distance before stopping again and alerting the user similar to a snooze alarm system of a clock radio.

Identifying the desired depth of penetration for pre-programmed implementations can be determined, for example, by knowing the typical size of the target tissue based upon the age and size of a patient or the actual size of the target tissue from pre-op radiographs, CT scans or MRI scans. A user can also manually estimate to approximately 70-80% depth travel through the proximal cortex, the medullar bone and close to or into the distal cortex prior to the automatic pre-programmed settings taking effect. For example, the user can manually estimate until a region of the bone is entered where a greater amount of control is desirable such as the distal cortex. At that stage, the axial drive of the instrument can be used to slowly proceed through that portion of the bone to the target location. A user can also proceed until a pop is felt or a change in speed can be heard in the drill, or as described above the second drop in power is shown on the GUI. This can be augmented by acceleration, power or torque measurements provided to the user. For example, as the drill bit penetrates to the very last layers of the distal cortex it can begin to accelerate with a burst of acceleration as it breeches the distal cortex completely, this can also be sensed as a change in torque and/or as a drop in power.

The instrument can provide its own auditory output to accentuate the sometimes subtle auditory changes caused by the drill bit. Upon reaching the predetermined target depth, axial movement of the device can automatically slow or stop while rotational movement can continue. However, that the user can manually override any pre-programmed limitations or automated controls by actuation/triggers on the device without changing hand positions to continue.

The control of the instruments described herein can also be adjusted manually by the user. For example, the user can change the thrust of the drive motor 30 by letting up or pressing down on the actuator 232. The user can also change the thrust of the instrument 10 by pushing down or letting up on the axial pressure being applied to the instrument 10. In an implementation, tissue resistance as compared to axial pressure on the instrument 10 applied by the user can cause/allow the relative position of the handle of the instrument 10 to feel as if it were backing out of the work as the tool 110 is axially extended from the instrument 10. This can require the user to apply additional axial pressure to drive the tool 110 through the tissue. The torque as related to the rotating tool 110 can also change during use of the instrument 10. This change provides feedback to the user who in turn can make appropriate adjustments to the axial and rotational movements as needed.

Energy, Pullout Strength and Implant Selection

The instruments described herein measure instantaneous torque and keep track of maximum insertion torque ("MIT"). Because insertion torque is related to the properties of the bone, such as its material strength and its bone density, it can be useful in providing diagnostic information related to the bone being drilled regionally, in real-time intra-operatively. Insertion torque alone does not consistently correlate with the pullout strength of the implant. The instruments described herein transform the insertion torque data into drilling energy in real-time which can be used to predict construct viability and hardware failure, i.e. pull-out strength.

Figure 8A:
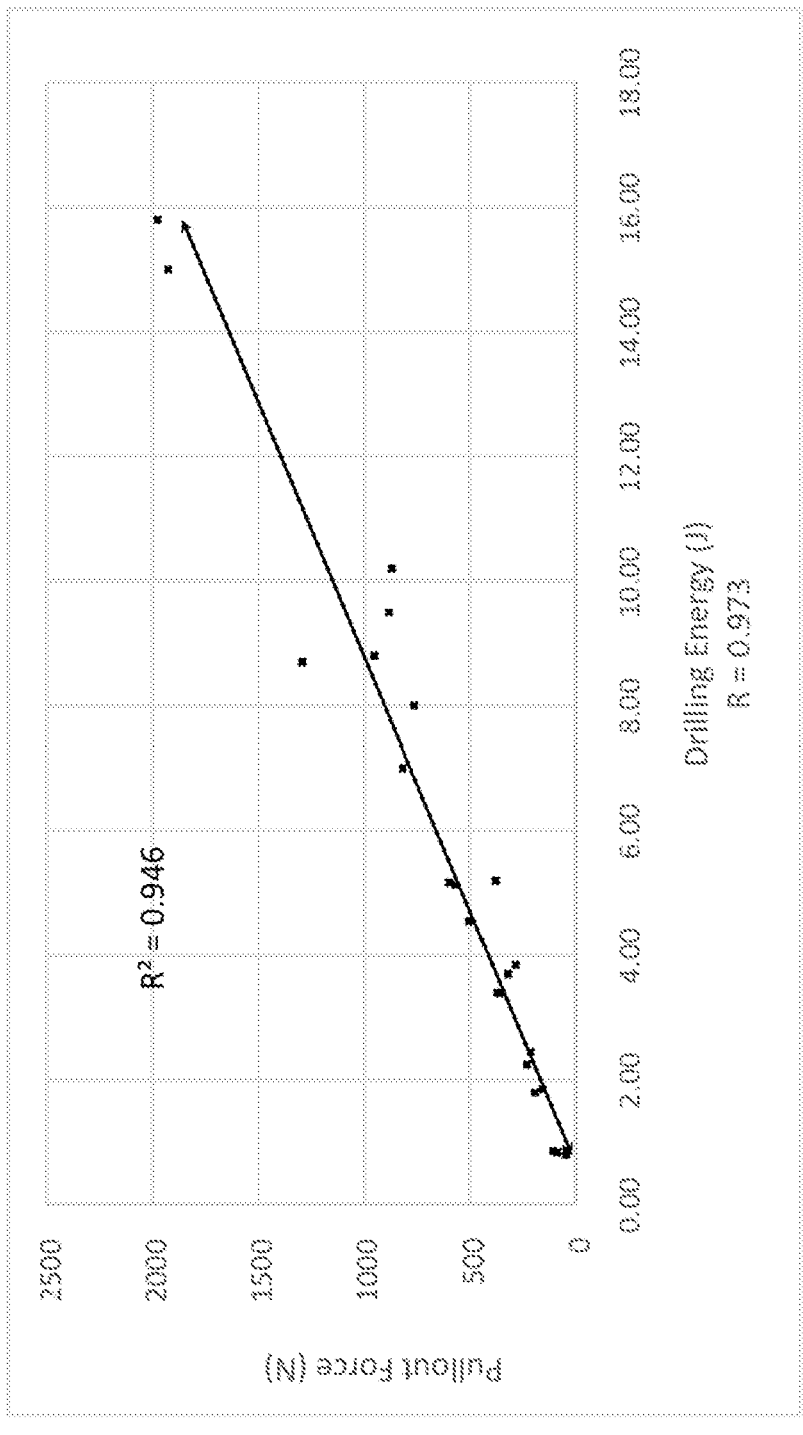
FIG. 8A illustrates the correlation between drilling energy and pullout strength of screws.
Figure 8B:
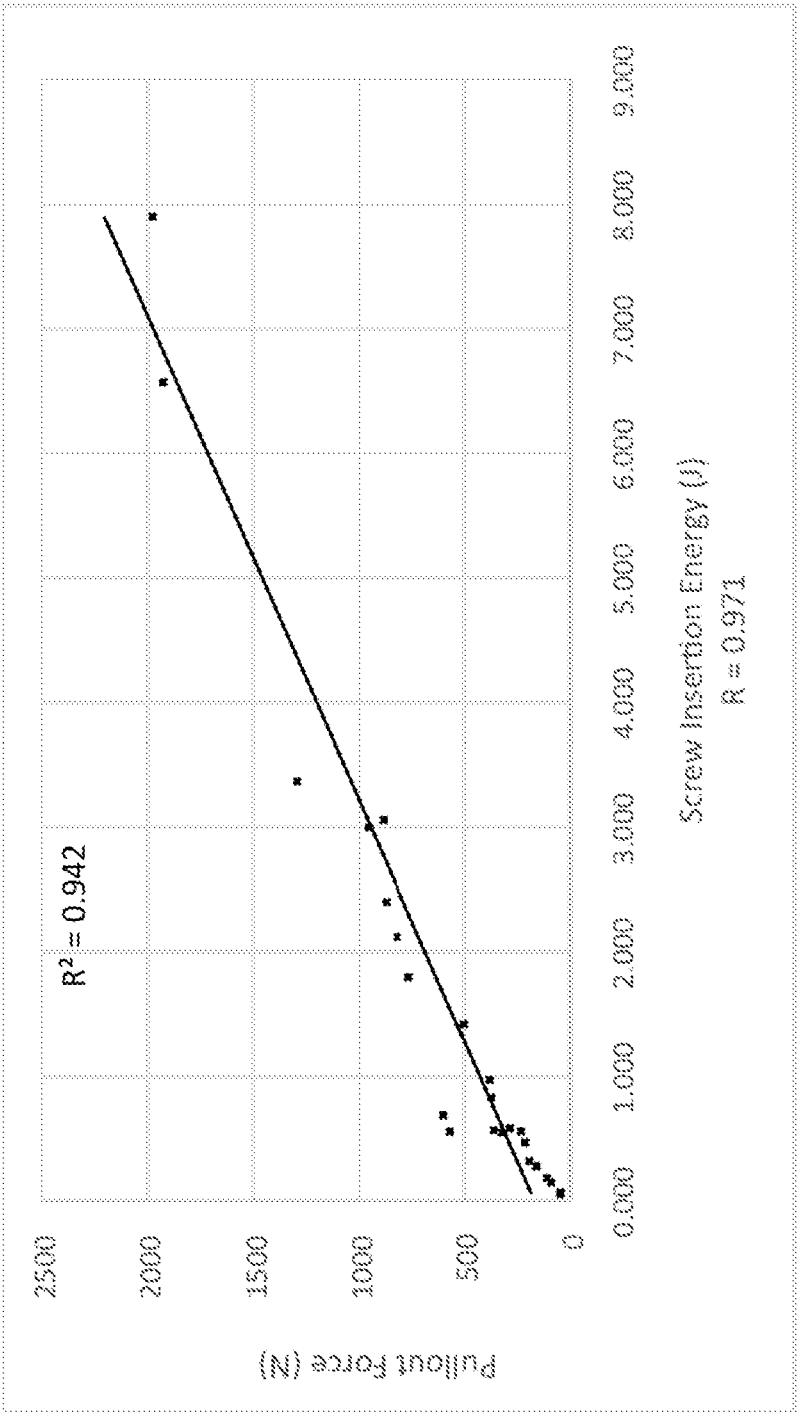
FIG. 8B illustrates the correlation between screw insertion energy and pullout strength of screw.
Figure 8C:
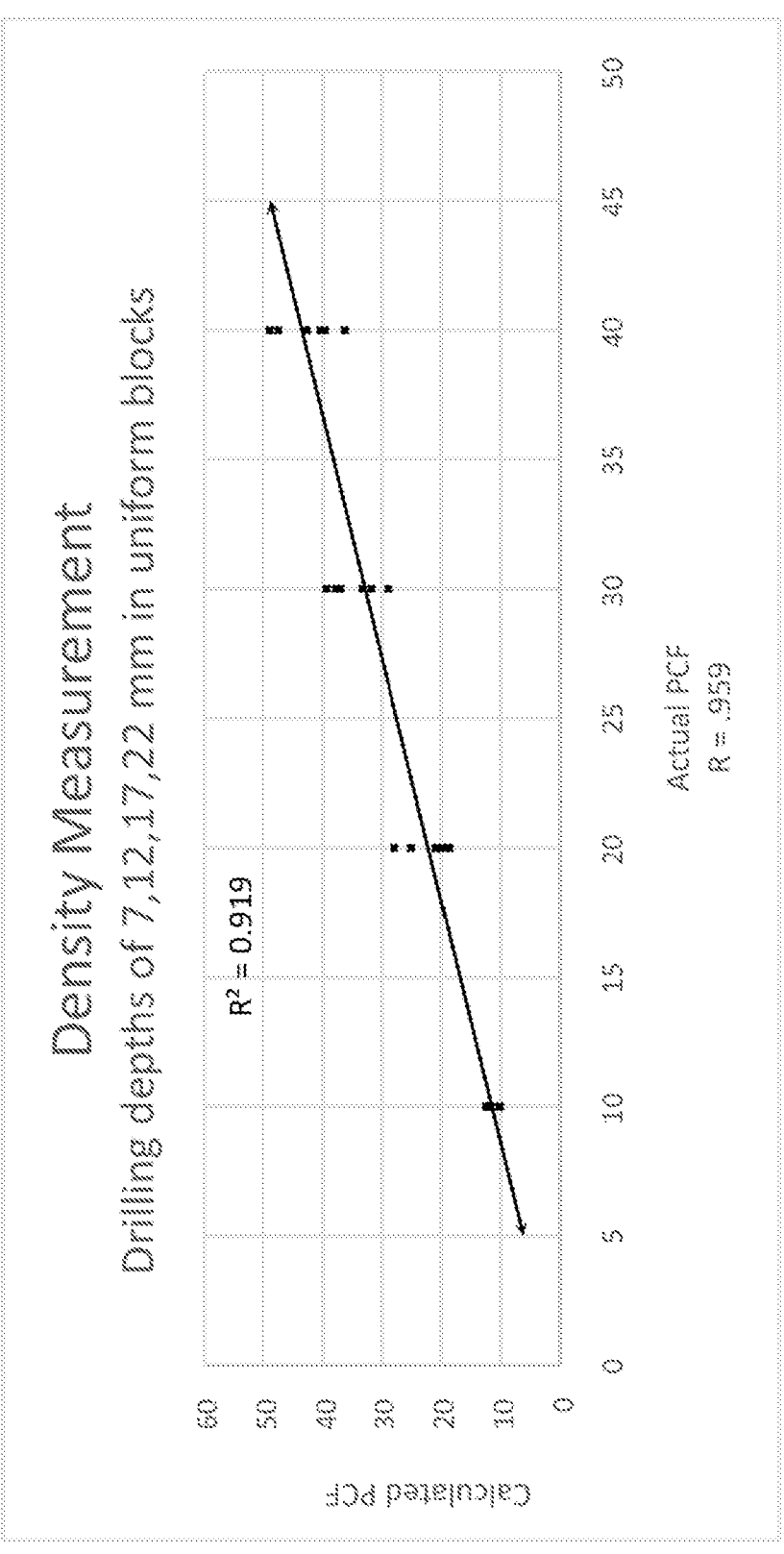
FIG. 8C illustrates the correlation between an algorithm that uses drilling energy to give a calculated pounds per cubic foot (PCF) ("calculated PCF") and actual PCF.

Pullout strength was assessed to evaluate potential construct strength. It was determined that regional bone strength determination correlates empirically with failure testing values. During material cutting, whether with a saw, drill bit, reamer, self-drilling screw or other tool, the energy that is expended by the tool to cut can be measured. The torque of the cutting tool can be measured as described herein, for example, using a torque sensor as a motor mount, a force sensor under a level arm connected to the motor mount, or a torque sensor on the bushing used to allow the exit of the working tool or tool chuck from the tool body. Torque data can be transformed in real-time into energy, for example, electronically using the known relationships between torque, power and energy. FIGS. 8A-8C illustrate the correlation between energy data and important strength parameters. FIG. 8A illustrates the correlation between drilling energy measured in joules shown on the x-axis and pullout force measured in Newtons is shown on the y-axis. The drilling energy of the pilot hole correlates directly with screw pullout strength and thus, regional material strength (r value of 0.96). As drilling energy increases so too does the force needed to pull the screw out. FIG. 8B illustrates the correlation between screw insertion energy and pullout strength of screws. FIG. 8C illustrates the correlation between an algorithm that uses drilling energy to give a calculated pounds per cubic foot ("calculated PCF") and actual PCF.

Conventionally, to select the appropriate fixation technique a user must make an educated guess. Even if the patient has bone density data obtained prior to the fracture, it may not be useful to estimate local material strength at the fracture fixation site. For example, dual energy X-ray absorptiometry (DEXA) scans are commonly used to measure bone density and monitor osteopenia or osteoporosis treatments. But a DEXA scan only measures bone density at two or three sites and cannot be performed acutely for a fracture patient. Also, the standardized regional measurements may not be relevant at the fracture site. Bone strength and density data at operative sites are key determinates of whether or not the implant construct will suffice. Implant choices can be made by guessing at the local bone strength and bone density at the operative site. For example, if the bone is thought to be soft and there is a fracture, operators will more often choose locking technology over non-locking technology. Since locking plates and screws are specifically for use in osteoporotic bone, this subjective system does not work very well. Locking plates are much more expensive and lead to more complications and patient complaints. In addition, insurance companies often will not reimburse the hospital for the additional cost of a locking plate if there is no evidence that it was necessary beyond a surgeon's assertion that the bone felt "spongy" or "soft" during drilling.

Figure 9:
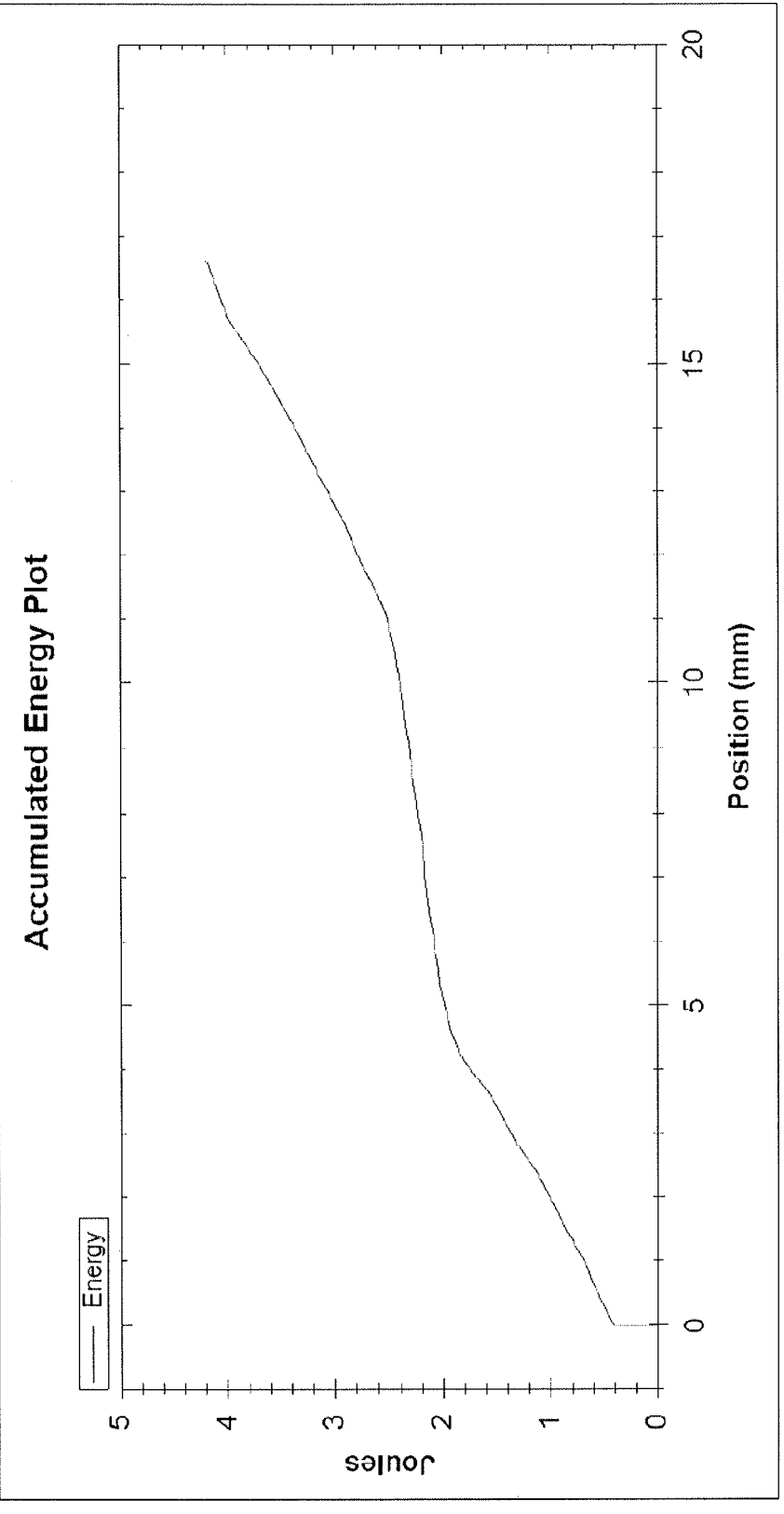
FIG. 9 illustrates an implementation of an accumulated energy plot for use with the graphical user interface of FIG. 7A.

The torque, power usage, and/or energy can be reported to the operator graphically and/or numerically and/or with gauges. In an implementation, the transformed accumulated drilling energy or total energy in joules can be tracked and displayed in real-time as well as stored. FIG. 9 illustrates an implementation of an accumulated energy plot illustrating that a total energy of 4.2 Joules was achieved after approximately 16 mm drilling. A surgeon can use the total energy value obtained after making a pilot hole to make an informed decision intra-operatively regarding the regional material strength, bone density and what sort of implant is indicated to prevent hardware failure. Because the data regarding the total energy required to drill the bore can be stored in the memory of the instrument or external computing device 600, the data can be provided as evidence, for example to insurers, that the bone was indeed soft or osteoporotic and that the more expensive locking plate was necessary.

Thus, the instruments described herein can correlate measuring energy with construct strength, for example pullout strength of screws. The instruments described herein can correlate drilling energy with implant strength to prevent hardware failure. The instruments described herein can correlate insertional energy of implants with success and/or failure of the implant. The instruments described herein allow for the measurement of accumulated energy during a material cutting process such as drilling, reaming or sawing or driving, such as driving in a screw or pin. The instruments described herein allows for the correlation of accumulated energy with hardware failure (pullout strength, toggle failure strength, etc.). The instruments described herein allow for the real-time determination of material strength. The instruments described herein allow for the correlation of tool power usage to material strength and for the correlation of tool torque to material strength.

It should be appreciated that although the various implementations of the instruments are described as incorporating a harp, for example to prevent plunge, the harp is not a requirement for the instruments to measure energy as described herein. Similarly, the instruments need not incorporate dual motors or a linear feed system in order to measure energy as described above for the correlation to and determination of material strength. For example, the instruments described herein can incorporate a screwdriver as a working tool for advancing screws into the bone. The drilling energy to drill the hole (with or without the guide harp) and the energy to put the screws into the bone (without the harp) can correlate with the strength of the bone (bone density) and the pullout strength of the screws.

Methods of Use

Below are examples of methods of using an instrument described herein. It should be appreciated that a variety of driving devices or working tools can be coupled to the instruments described herein. Description related to guides on a drilling device having a drill bit coupled thereto is not intended to be limited to only drills and drilling bores. Rather, the instruments and guides can be used to saw or drive into tissues as described herein.

It should be appreciated that any of the instruments described herein can be coupled to robotic arms or robotic systems or other computer-assisted surgical systems in which the user uses a computer console to manipulate the controls of the instrument. The computer can translate the user's movements and actuation of the controls to be then carried out on the patient by the robotic arm. Robotics can provide real-time pre- and inter-operative tactile and/or auditory feedback along with visualization, such as three-dimensional modeling. The robotic system can have an articulated endowrist at the end of two or more "working" arms configured to be inserted through a small portal. A stable, camera arm with two lenses (allowing stereoscopic images) can be also inserted through another small portal. The end-effectors can manipulate instruments and can have various degrees of freedom. The user can control the robot through a console placed in the operating room, allowing control of both the external and internal surgical environments. The user's interface can have instrument controllers that can filter tremor and decrease the scale of motion. Foot pedals can expand the user's repertoire, allowing tissue coagulation and irrigation. Visual feedback can be through a stereoscopic display. Robotic systems to which the devices disclosed herein can be coupled include the Haptic Guidance System or RIO® Systems (MAKO Surgical Corp, Ft. Lauderdale, Fla.) and the da Vinci® Surgical Systems (Intuitive Surgical, Sunnyvale, Calif). Other surgical robots can be considered as well including the Robot-Assisted Micro-Surgery (RAMS) system (MicroDexterity Systems, Inc.), NeuroArm® (University of Calgary), Zeus® Surgical robots, SpineAssist (Mazor Surgical Technologies, Israel), ROBODOC and ORTHODOC (Curexo Technology Corp., Fremont, Calif), ACROBOT (Acrobot, Elstree, UK), Path-Finder (Prosurgics Ltd., Loudwater, High Wycombe, UK), and Laprotek system (Hansen Medical, Inc.). Other robotic arms can be used with the instruments described herein such that the instrument can be independently controlled by the robot as opposed to direct manipulation by the user.

In one implementation of the method, the user can dissect tissue down to the bone and create a field large enough to put against the bone the working tool 110 or distal guide 170 or an implant attached to the distal guide 170. Screws can be placed across fractures without any other implants or a plate can be fixed across the fracture by bone screws. The screws can lock into the plate and bone. When a plate is to be used, the user can create a field large enough to place the plate. Alternatively, the plate can be inserted through a small incision such that the user can slide it along the surface of the bone in combination of blunt dissection of the tissue along the way (i.e. subcutaneous plate). The screws can be placed, for example using a radiograph to find the holes in the plate, through small incisions through the skin with dissection down to the bone. The surrounding tissue can be protected using retractors, a guide through which the working tool is inserted, attachable guides placed on the instrument and the like. If a distal guide 170 is used, the length of the guide 170 can be accounted for in the depth measurement. If a guide 170 attached to an implant is used, the depth can be automatically or manually zeroed. For example, if a plate is used the thickness of the plate can be automatically or manually accounted for in the zeroing.

The working end of the instrument 10, with or without a distal guide 170, can be placed next to the exposed and dissected bone and the instrument zeroed. The instrument can be zeroed on a display or user interface 505 of the instrument 10 or on a user interface 605 of an external computing device 600. Alternatively, the user can extend a few millimeters of the working tool 110 to engage the bone and drill a counter-sink or pilot hole prior to zeroing the instrument 10. Where a fixation plate is used, the plate can be placed next to the bone and the drill end placed snug to the plate. Alternatively, some plates have guides that interface such that the instrument is directed at a selected angle. The instruments disclosed herein can be made such that they attach to or freely engage these types of distal guides 170.

The user can apply pressure axially, for example, within a desired range of axial pressures, and engage first the rotational drive motor 60 to the desired speed. The user can proceed to engage the axial drive motor 30 either continuously or incrementally, depending upon the assumed material strength and bone density and preference of the user. The drilling can continue through the cortical bone, through the medullary canal or cancellous bone, into and through the distal cortical bone. The travel of the tool through various layers of bone can be tracked as described herein, for example, as a plot of power vs. distance. The axial movement can be stopped, either manually by the user or electronically by the software of the instrument, and the user can remove the working tool 110 by reversing the axial drive motor 30 or by pulling back on the instrument 10. The rotational drive motor 60 can be left engaged and in the forward direction to facilitate clearing the hole created. The total depth of the bore can be displayed, for example as a number or as a plot such as a plot of power as a function of depth. Similarly, the accumulated energy in joules can be displayed. Based on this information, the user can select the proper construct for implantation, such as a screw with or without a locking plate or a non-locking plate. The construct can be implanted using a screw driver or the like. In another method, the user can perform a unicortical procedure wherein the working tool is stopped prior to some other endpoint such as before or after a growth plate or before or after the distal cortex.

In some implementations, an instrument 10 can be set against exposed bone or, if used, the fracture fixation plate or other type of implant such as a joint prosthetic. The appropriate zero-depth position can be determined automatically. Once the user activates the trigger 232, the guide harp 300 retracts in the proximal direction (arrow P) and the working tool 110 can extend through the distal guide 170. The working tool 110 can engage the work and bore into the work as the user applies pressure to the instrument 10 and keeps it engaged with the work. The amount of pressure applied by the guide harp 300 and/or the working tool 110 can be displayed, for example on the external computing device 600. The working tool 110 can drill into the bone by the amount the guide 300 retracts. The guide 300 retraction can be measured instantaneously and shown on a display, for example a display positioned at the back of the instrument 10 or on the external computing device 600. The automatic determination of the zero-position whether set against bone or against a fracture fixation plate can depend upon algorithms related to the way the guide 170 sets against the bone or the plate and the thickness of the plate. These variables can be unique to each plating system and set of guides. The depth of the travel of working tool 110 into the work, and/or the instantaneous torque, torque curve or accumulated energy, can be measured and shown on the display simultaneously and instantaneously as the working tool 110 moves axially in a distal direction and penetrates the work. Once the desired depth of penetration is reached, the reverse trigger 234 can be actuated to cause both of the drive motors 30, 60 to reverse their direction. The action of the axial drive motor 30 can cause the guide harp 300 to move in an axial direction away from the body 20 of the instrument 10 in a distal direction such that the axial movement pushes the instrument body 20 away from the work and draws the tool 110 out of the work. Alternatively, the operator can pull the tool 110 from the work with the instrument either on (in any direction) or off. In some implementations, the controller 510 controls the guide harp 300 based, in part, upon data from the force sensor 66. The controller 510 retracts the guide harp 300 in the proximal direction (arrow P) at a pace (which can be variable) such that a constant force against the work is maintained at the working tool 110. For example, the sensor can determine that the operator has fallen below the force minimum for the guide harp 300. If the guide harp 300 pressure drops below a first threshold (e.g. 10N) a warning can be signaled by the controller. If the guide harp 300 drops below a second threshold (e.g. 5N) the controller can turn off both motors.

The instruments described herein can incorporate dual force technology such that forces at the working tool 110 as well as forces at the guide harp 300 can be measured and used to control the instrument to maintain optimal working tool conditions. As mentioned above, the controller 510 can be used to retract the guide harp 300 and keep the working tool 110 at a constant force against the work during use. A cutting tool in order to cut has an optimal specific force at a given rpm. When working with harder material, keeping constant linear speed can result in a significantly increased force which can cause the tool to become inefficient resulting in increased energy to do the same work. The increased energy dissipates as heat transferred onto the tissue, which for bone is dangerous in that it can cause bone damage and death. When working with softer material, keeping a constant linear speed can result in a decreased force which also can cause the tool to become inefficient. More time is spent to go through the material increasing the dissipated heat into the tissue. When drilling with typical instruments known in the art, the operator must push relatively hard to go through the bone to avoid spinning the drill bit in place leading to bone burning. The harder an operator pushes with typical instruments, the more plunge that occurs upon breakthrough. However, if an operator lightens up on the force applied such as to avoid plunging, the risk of thermal injury and burn increases. Dual force technology of the instruments described herein allows for constant force work to be performed maintaining the cutting tool in its sweet spot such that the optimal specific force for cutting at a given rpm is maintained. It should be appreciated that the dual force technology works whether the instrument is being used manually by an operator or using a robotic arm.

Figure 10:
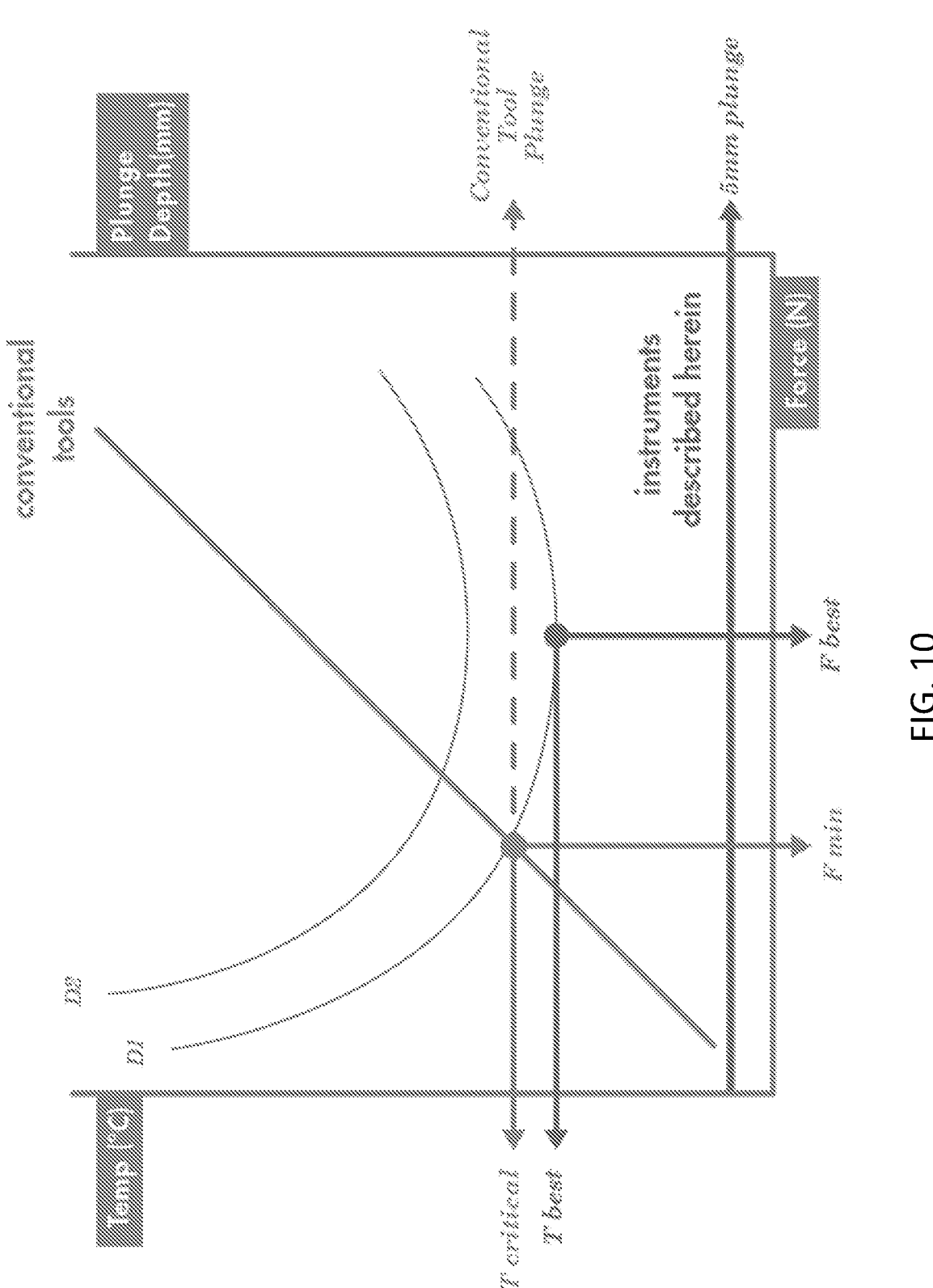
FIG. 10 illustrates non-linear temperature vs. force curves for conventional cutting tools.

FIG. 10 illustrates non-linear temperature vs. force curves that are characteristic of conventional cutting tools such as drill bits (D1, D2). FIG. 10 demonstrates the relationship between applied linear force and plunge depth that results upon use of such conventional drills. Fmin is the minimal force that gives you the desired Tcritical (highest temperature allowed before tissue burn occurs) resulting in the Plunge min. The temperature vs. force curves (D1 and D2 curved lines in FIG. 10) for such cutting tools are non-linear. Standard drills known in the art generally have a Plunge min that is between 5 mm and 15 mm. For example, if force is lessened reducing the Fmin, temperature rises due to inefficient spinning of the drill bit without forward penetration through the material. This higher than Tcritical temperature can mean increased risk for burning and damage to tissues (i.e. nerves and bone). Although the goal during drilling is to keep the temperature of the tissue low, the Tcritical can vary depending on the safety margin desired by a user. For example, if bone burns at 50° C., the Tcritical is less than this temperature within a particular safety margin, for example, within 0.1, 0.2, 0.3, 0.4, 0.5, 1.0, 2.0 degrees and so on under the temperature at which the bone (or other relevant tissue) burns. In some implementations, the Tcritical achieved by the Fmin is 49.9° C. such that the resulting Plunge min is approximately 5 mm-6 mm. In another implementation, the Tcritical achieved by the Fmin is 48° C. such that the resulting Plunge min is near 10 mm. Thus, Plunge min is the result of Fmin and Tcritical. It should be appreciated, however, that the relationships between Tcritical, Fmin and Plunge min of these conventional cutting tools can vary depending upon the drill bit type, drill bit diameter, hardness of material, and quality of the tool. Also, most operators tend to lighten up the force they apply to the drill when nearing an end of a target to keep the plunge to a minimum. This causes the Fmin to drop and a momentary rise in temperature above the Tcritical.

The instruments described herein break the directly proportional relationship between applied linear force and plunge depth seen in conventional cutting tools. Rather than following the slope of the plunge curve (straight line in FIG. 10) where plunge depth is a function of force applied, the instruments described herein cause the plunge curve to flatten as force increases such that plunge depth is controlled to less than about 0.5 mm. Because plunge depth is no longer a function of force on the working tool as shown in conventional cutting tools, the instruments described herein incorporating a harp guide that prevents plunge allow for a much higher cutting force to be maintained throughout use without an associated increase in plunge. It should be appreciated that the plunge curve flattens out using the instruments described herein whether the drop in force results in the controller automatically shutting off the motors or whether the operator identifies the drop in force, for example, by reading a graphical representation of the force on a user interface and shuts off the motors. Either implementation results in the guide harp 300 no longer retracting upon the second drop in power upon breakthrough thus, preventing the working tool from further penetration. It should also be appreciated that the instruments described herein can sense temperature of the work, for example, by sensing temperature of the drill bit and/or instrument temp. Temperature sensing can also be performed such as by incorporating a thermal camera.

Aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive signals, data and instructions from, and to transmit signals, data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

While this specification contains many specifics, these should not be construed as limitations on the scope of what is claimed or of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An instrument for penetrating tissue, the instrument comprising
   a body having a forward end and a rear end;
   a working tool connected to the forward end of the body;
   one or more motors housed in the body; and
   a guide harp, the guide harp comprising one or more rods, wherein the one or more rods of the guide harp extend beyond the rear end of the body, wherein the one or more rods of the guide harp are coupled to the body at the rear end of the body by extending through a rear guide, the rear guide comprising a rear housing cover.

2. The instrument of claim 1, further comprising a distal guide element, wherein the distal guide element is withdrawn revealing a length of the working tool extending beyond a distal engagement end of the instrument.

3. The instrument of claim 1, wherein the rear guide houses a harp feed guide sub-assembly, the harp feed guide sub-assembly engages the one or more rods via threads or step gear cuts on at least a portion of a length of the one or more rods.

4. The instrument of claim 1, wherein the one or more rods of the guide harp extend through the rear guide and extend out the rear housing cover of the rear guide.

5. The instrument of claim 1, wherein the guide harp comprises two rods.

6. The instrument of claim 1, at least two rods of the one or more rods are telescoping rods and at a first time point are in a first position extending out of the rear housing cover and at a second time point are in a second position not extending out of the rear housing cover.

7. An instrument for penetrating tissue, the instrument comprising
   a body having a first end and a proximal end;
   a working tool connected to the first end of the body; and
   one or more motors housed in the body wherein the one or more motors comprises a rotational drive motor having a drive shaft wherein the rotational drive motor and drive shaft form a motor sub-assembly, the motor sub-assembly having a sensor and a motor mount wherein one or more motors is mounted to the body by a torque sensor, the torque sensor having a motor mount configured to attach the one or more motors to the body and wherein the motor mount comprises one or more guide pins configured to interface with a harp feed drive sub-assembly.

8. The instrument of claim 7, wherein the motor sub-assembly is suspended between a bearing at the first end of the body and the motor mount coupled to the proximal end of the body such that the sensor is positioned between the rotational drive motor and the motor mount and does not contact the body directly.

9. The instrument of claim 7, wherein the drive shaft extends through a bushing within the first end of the body.

10. The instrument of claim 9, wherein the sensor is an axial force sensor incorporated within the bushing.

11. The instrument of claim 7, wherein the drive shaft of the rotational drive motor extends through the first end of the body and couples with a rotatably-driven coupler or rotatably-driven coupler extension.

12. The instrument of claim 7, the harp feed drive sub-assembly is coupled to the proximal end of the body by at least one guide bushing the at least one guide bushing coupled with guide pins of a motor mount sub-assembly.

13. An instrument for penetrating tissue, the instrument comprising
a body;
a working tool connected to the body;
a guide harp, the guide harp comprising one or more rods wherein the one or more rods of the guide harp extend beyond a rear end of the body;
one or more motors housed in the body;
a sensor housed in the body, wherein the one or more motors is mounted to the body by the sensor;
a display displaying a processed signal wherein the processed signal is representative of a combination of torque, energy, and power.

14. The instrument of claim 13, wherein the processed signal is accumulated energy.

15. The instrument of claim 14, wherein the accumulated energy is displayed as a function of position or as a function of time.

16. The instrument of claim 13, wherein the processed signal is power.

17. The instrument of claim 16, wherein the power is displayed as a function of time or as a function of depth.

18. The instrument of claim 13, wherein the processed signal provides information regarding penetration of the working tool and when to stop penetration of the working tool.

* * * * *